(12) United States Patent
Aguilar et al.

(10) Patent No.: US 12,100,506 B2
(45) Date of Patent: Sep. 24, 2024

(54) CONTROL SYSTEMS AND METHODS

(71) Applicant: SHANGHAI UNITED IMAGING HEALTHCARE CO., LTD., Shanghai (CN)

(72) Inventors: Walter Arturo Aguilar, Houston, TX (US); Johannes Stahl, Houston, TX (US); Shaomin Xiao, Shanghai (CN); Yaoming Shi, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 757 days.

(21) Appl. No.: 17/129,934

(22) Filed: Dec. 22, 2020

(65) Prior Publication Data

US 2021/0225501 A1  Jul. 22, 2021

Related U.S. Application Data

(63) Continuation of application No. PCT/CN2020/073933, filed on Jan. 22, 2020.

(51) Int. Cl.
*G16H 40/60* (2018.01)
*A61B 6/00* (2006.01)
(Continued)

(52) U.S. Cl.
CPC .......... *G16H 40/60* (2018.01); *A61B 6/0407* (2013.01); *A61B 6/4417* (2013.01); *A61G 13/02* (2013.01);
(Continued)

(58) Field of Classification Search
CPC ........ G16H 40/60; G16H 20/40; G16H 30/20; G16H 40/40; G16H 40/63; A61B 6/0407;
(Continued)

(56) References Cited

U.S. PATENT DOCUMENTS 5,615,430 A   4/1997   Nambu et al.
9,498,167 B2  11/2016  Mostafavi et al.
(Continued)

FOREIGN PATENT DOCUMENTS

CN   101355505 A   1/2009
CN   102553080 A   7/2012
(Continued)

OTHER PUBLICATIONS

The Extended European Search Report in European Application No. 20915537.3 mailed on Dec. 13, 2022, 8 pages.
(Continued)

*Primary Examiner* — Mohammad Ali
*Assistant Examiner* — Sheela Rao
(74) *Attorney, Agent, or Firm* — METIS IP LLC

(57) ABSTRACT

The present disclosure provides systems for controlling movement of a table supporting an object. The system may include: a first control sub-system configured to generate a first control instruction; a second control sub-system configured to generate a second control instruction; a table control sub-system operably coupled to the table; and a master controller configured to receive the first control instruction from the first control sub-system, or the second control instruction from the second control sub-system, generate a third control instruction based on the first control instruction or the second control instruction, and transmit the third control instruction to the table control sub-system. The table control sub-system may be configured to generate a control signal based on the third control instruction, and cause the table to move based on the control signal.

12 Claims, 11 Drawing Sheets

(51) Int. Cl.
    *A61B 6/04*     (2006.01)
    *A61G 13/02*     (2006.01)
    *G05B 19/042*     (2006.01)
    *G16H 20/40*     (2018.01)
    *G16H 30/20*     (2018.01)
    *G16H 40/40*     (2018.01)

(52) U.S. Cl.
    CPC ......... *G05B 19/0421* (2013.01); *G16H 20/40*
    (2018.01); *G16H 30/20* (2018.01); *G16H*
    *40/40* (2018.01); *G05B 2219/2231* (2013.01);
    *G05B 2219/25039* (2013.01)

(58) Field of Classification Search
    CPC ....... A61B 6/4417; A61B 6/032; A61B 6/037;
    A61B 6/54; A61G 13/02; A61G 13/0018;
    A61G 13/10; A61G 2203/10; G05B
    19/0421; G05B 2219/2231; G05B
    2219/25039; G05B 15/02; G05B
    2219/2652; G05B 19/41865; A61N
    5/1049; A61N 5/107; A61N 2005/1061;
    A61N 2005/1063; A61N 2005/1097
    See application file for complete search history.

(56) References Cited

U.S. PATENT DOCUMENTS

| | | |
|---|---|---|
| 2003/0176779 A1 | 9/2003 | Ghelmansarai |
| 2006/0215817 A1 | 9/2006 | Watanabe |
| 2012/0142357 A1 | 6/2012 | Aminaka |
| 2016/0089212 A1 | 3/2016 | Balicki et al. |
| 2017/0201979 A1 | 7/2017 | Murphy et al. |
| 2017/0296846 A1* | 10/2017 | Ju .................. A61N 5/1049 |
| 2017/0359275 A1* | 12/2017 | Puthillathe ........... H04L 49/351 |
| 2019/0090838 A1* | 3/2019 | Tanaka .................. A61B 6/542 |
| 2019/0103989 A1* | 4/2019 | Kida .................... B25J 9/1682 |
| 2019/0209864 A1 | 7/2019 | Stahl et al. |
| 2022/0016443 A1 | 1/2022 | Zhou et al. |

FOREIGN PATENT DOCUMENTS

| | | |
|---|---|---|
| CN | 104056367 A | 9/2014 |
| CN | 105983183 A | 10/2016 |
| CN | 107569783 A | 1/2018 |
| CN | 207354303 U | 5/2018 |
| CN | 109453472 A | 3/2019 |
| JP | 3639183 B2 | 4/2005 |

OTHER PUBLICATIONS

International Search Report in PCT/CN2020/073933 mailed on Oct. 28, 2020, 5 pages.

Written Opinion in PCT/CN2020/073933 mailed on Oct. 28, 2020, 4 pages.

First Office Action in Chinese Application No. 202080003207.8 mailed on Mar. 25, 2022, 14 pages.

* cited by examiner

CONTROL SYSTEMS AND METHODS

CROSS-REFERENCE TO RELATED APPLICATIONS

This present application is a continuation of International Application No. PCT/CN2020/073933, filed on Jan. 22, 2020, the contents of which are hereby incorporated by reference.

TECHNICAL FIELD

The present disclosure generally relates to control technology, and more particularly to systems and methods for controlling movement of a component shared by multiple devices.

BACKGROUND

A table for supporting an object is widely used in an imaging device and/or a treatment device. Devices with different functionalities can be combined or integrated to facilitate the diagnosis and/or treatment of the object. In this case, the table supporting the object can be shared by two or more devices, and controlled by any one of the devices. To this end, a coordinated control of the table between the devices is needed. For example, a combination of an imaging device and a treatment device, which forms a therapeutic apparatus, may need to have a coordination mechanism for a dynamic control of the table between imaging and radiation therapy treatment applications. Generally, the transfer of the control of the table between the imaging device and the treatment device needs to be coordinated and with a low latency. Therefore, it is desirable to develop systems and methods for controlling a table shared between two or more functionalities with a relatively high accuracy and a relatively low latency.

SUMMARY

In one aspect of the present disclosure, a system for controlling movement of a table supporting an object is provided. The system may include: a first control sub-system configured to generate a first control instruction; a second control sub-system configured to generate a second control instruction; a table control sub-system operably coupled to the table; and/or a master controller configured to receive the first control instruction from the first control sub-system, or the second control instruction from the second control sub-system, generate a third control instruction based on the first control instruction or the second control instruction, and/or transmit the third control instruction to the table control sub-system. The table control sub-system may be configured to generate a control signal based on the third control instruction, and/or cause the table to move based on the control signal.

In some embodiments, the first control sub-system may be further configured to transmit first clock synchronization information associated with the first control sub-system to the master controller. The master controller may be further configured to update time information associated with the master controller according to the first clock synchronization information.

In some embodiments, the second control sub-system may be further configured to transmit second clock synchronization information associated with the second control sub-system to the master controller. The master controller may be further configured to update time information associated with the master controller according to the second clock synchronization information.

In some embodiments, the first control sub-system may be operably coupled to a first device. The second control sub-system may be operably coupled to a second device. The table may be configured to move between the first device and the second device.

In some embodiments, the first device may be an imaging device, and the second device may be a treatment device. Alternatively, the first device may be an imaging device of a first modality, and the second device may be an imaging device of a second modality, the first modality being different from the second modality.

In some embodiments, the first control sub-system may be operably connected to the second control sub-system via a virtual table motion controller. The virtual table motion controller may be configured to relay the first control instruction from the first control sub-system to the second control sub-system. The second control sub-system may be configured to relay the first control instruction to the master controller.

In some embodiments, the first control sub-system and the master controller may have a point-to-point connection.

In some embodiments, the point-to-point connection may include a peripheral component interconnect express (PCIE) connection.

In some embodiments, a latency time between the master controller and the first control sub-system may be less than 10 microseconds.

In some embodiments, the table control sub-system may be further configured to determine movement information of the table; and/or transmit the movement information to the master controller.

In some embodiments, the master controller may be further configured to transmit the movement information to the second control sub-system.

In some embodiments, the second control sub-system may be further configured to determine whether the table is under a control of the first control sub-system; and/or in response to determining that the table is under the control of the first control sub-system, transmit the movement information to the first control sub-system via the point-to-point connection.

In some embodiments, the first control sub-system may be operably connected to the master controller via a virtual table motion controller. The virtual table motion controller may be configured to relay the first control instruction from the first control sub-system to the master controller bypassing the second control sub-system.

In some embodiments, the system may include a switch mechanism configured to cause the master controller to switch between a first functional connection with the first control sub-system and a second functional connection with the second control sub-system.

In some embodiments, the switch mechanism may be further configured to switch control of the table between the first control sub-system and the second control sub-system based on a control command from the first control sub-system or the second control sub-system, or a workflow.

In some embodiments, the table control sub-system may be further configured to determine movement information of the table; and/or transmit the movement information to the master controller.

In some embodiments, the master controller may be further configured to: in response to determining that the control of the table is switched to the first control sub-system, transmit the movement information to the first control sub-system; or in response to determining that the control of the table is switched to the second control sub-system, transmit the movement information to the second control sub-system.

In another aspect of the present disclosure, a system for imaging and treating an object is provided. The system may include: an imaging device configured to generate an image of the object; a treatment device configured to treat the object based on the image. The imaging device may include a first control sub-system configured to generate a first control instruction. The treatment device may include a second control sub-system configured to generate a second control instruction, a table configured to support the object, a table control sub-system that is operably coupled to the table and configured to control the table to move, and a master controller configured to facilitate communication between at least one of the imaging device or the treatment device, and the table control sub-system. The table may be movable relative to the imaging device according to the first control instruction, or relative to the treatment device according to the second control instruction. The first control sub-system may be operably connected to the treatment device. The first control sub-system and the master controller may have a point-to-point connection.

In some embodiments, the system may further include: a virtual table motion controller configured to relay the first control instruction from the first control sub-system to the second control sub-system. The virtual table motion controller may be configured to tunnel the first control instruction of a first protocol into a packet of a second protocol. The second control sub-system may be further configured to decode the packet. The master controller may be further configured to relay the decoded packet to the table control sub-system.

In another aspect of the present disclosure, a system for imaging and treating an object is provided. The system may include: an imaging device configured to generate an image of the object; a treatment device configured to treat the object based on the image; a table configured to support the object; a table control sub-system that is operably coupled to the table and configured to cause the table to move under control of the imaging device or the treatment device; a master controller operably connected to the table control sub-system. The imaging device may include a first control sub-system configured to generate a first control instruction for controlling the table. The treatment device may include a second control sub-system configured to generate a second control instruction for controlling the table. The system may include a switch mechanism on the second control sub-system configured to switch control of the table between the imaging device and the treatment device.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein:

FIG. 9 is a block diagram illustrating a third exemplary system of the medical apparatus according to some embodiments of the present disclosure; and.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, section or assembly of different level in ascending order. However, the terms may be displaced by another expression if they achieve the same purpose.

Figure 2:
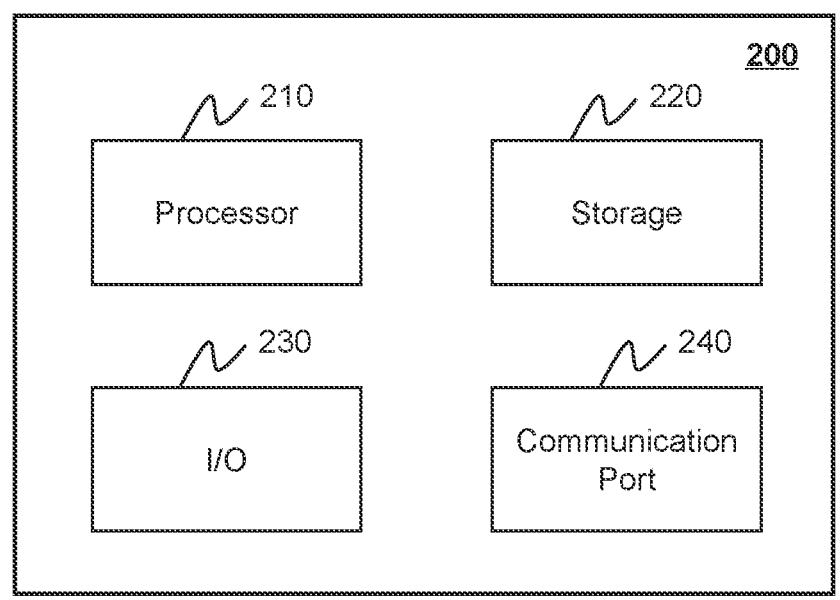
FIG. 2 is a schematic diagram illustrating exemplary hardware and/or software components of an exemplary computing device on which the one or more processing devices may be implemented according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., processor 210 as illustrated in FIG. 2) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

The flowcharts used in the present disclosure illustrate operations that systems implement according to some embodiments of the present disclosure. It is to be expressly understood the operations of the flowcharts may be implemented not in order. Conversely, the operations may be implemented in inverted order, or simultaneously. Moreover, one or more other operations may be added to the flowcharts. One or more operations may be removed from the flowcharts.

The present disclosure relates to systems and methods for controlling the movement of a component shared by multiple devices, e.g., a table supporting an object shared by two or more devices. Merely by way of example, in a computed tomography (CT)-radiotherapy (RT) apparatus, the table may support the object in an RT device and in a CT device. In the combined CT-RT (also referred to as CT-Linac) apparatus for radiotherapy, the two devices (i.e., CT and RT) may share the same table, and collaboratively implement a dynamic control of the table for CT imaging and for radiotherapy treatment. In CT imaging, the table may need to be precisely controlled since the scanning and acquisition of images by an X-ray generator and an image detector of the CT device needs to be synchronized with the position of the table with a relatively high resolution (e.g., a micro-second resolution) and accuracy. In the case of the combined CT-RT apparatus, the control of the table may be shared between the RT device and the CT device, and the RT device and the CT device may need to have control of the table at different times in the imaging and therapy stages of a treatment process. For example, prior to receiving radiation therapy, the object may be imaged using the CT device to detect a position of a target volume (e.g., a tumor or lesion) or to detect whether a shape and/or size of the target volume has changed in comparison with a treatment plan. If the shape and/or size of the target volume has changed, the treatment plan may need to be modified to adapt to the current conditions of the target volume. This process may be referred to as adaptive radiation therapy (ART). If there is no significant change in the target volume, the image generated by the CT device may be used for detecting the current position of the target volume, and the object can be positioned on the table with relatively high precision for treatment. Because the imaging process and the treatment process can be performed with the object on the same table, and the placement of the object on the table does not change, there may be a relatively high level of confidence in the placement of the object relative to the treatment beam of the RT device.

In a CT device, the X-ray generator and the image detector are placed opposite from each other on a rotating gantry, and the rotation speed and image acquisition may be synchronized with the position of the table to capture images or slices that cover the target volume. The synchronization of the rotating gantry and the table may need to be with micro-second precision to be able to reconstruct a target image with a relatively high resolution and integrity. The control of the table position in the CT device may be performed by a same controller (i.e., a CT controller) that controls the position of the rotating gantry. The CT controller may synchronize the table motion with the gantry rotation, the X-ray generation, and/or image detection and processing. In a CT-RT apparatus, where the table is shared by the RT device and the CT device, the transfer of the control of the table between an RT controller and the CT controller may need to be coordinated and with a low latency.

In some embodiments, the table may be directly controlled by a table controller (e.g., a longitudinal axis motor controller). In some embodiments, the table controller may communicate with or receive control commands from the CT controller or the RT controller so that the CT controller or the RT controller can take control of movement of the table. In some embodiments, the CT device may be directly integrated into a currently available RT device, and the CT controller may communicate with the table controller via the RT controller. Therefore, the communication between the RT controller and the table controller may inherently have a low latency, but the communication between the CT controller and the table controller may have a relatively high latency. Alternatively, in some embodiments, the RT device may be directly integrated into a currently available CT device, and the RT controller may communication with the table controller via the CT controller. Therefore, the communication between the CT controller and the table controller may inherently have a low latency, but the communication between the RT controller and the table controller may have a relatively high latency. Because the table is shared by two devices, a conventional communication between the devices for controlling the movement of the table, e.g., by routing control commands of the table through one or more intermediary relay controllers (e.g., the CT controller, the RT controller, the table controller), may take too much time and introduce an unwanted latency, thereby reducing control precision and/or control efficiency of the control system.

According to some embodiments of the present disclosure, one or more control mechanisms are used to relay commands generated by the CT controller or RT controller to a table controller of the table with a relatively low latency. Merely by way of example, the control mechanism of some embodiments of the present disclosure may include a tunneling of communication packets generated by the CT controller via a high-speed communication interface to a virtual master node. The communication packets may include control commands. The virtual master node may be configured to relay the communication packets to the table controller that is responsible for the longitudinal table motion synchronized with image acquisition. To the table controller, the virtual master node may be a master, and the virtual master node may relay to the table controller one or more control commands from the CT controller when the apparatus is in a CT application mode or from the RT controller when the apparatus is in an RT application mode. With this mechanism, if the CT controller is controlling the table motion, the RT controller may be passive relative to the communication between the CT controller and the table controller. If the CT controller relinquishes control, the RT controller may take control of the table controller. This mechanism may allow for minimal changes to the CT controller and the RT controller. Besides, when the CT-RT apparatus switches from RT control of the table to CT control of the table (or vice versa), the switch may be transparent to the RT controller and CT controller. With this mechanism, no conflict may occur, since both the RT controller and CT controller behave like masters when they need to control the table. A switching mechanism may be realized by one or more virtual communication nodes that tunnel the communication packets with high speed so that there is little latency. It should be noted that the transfer of the control of the table may have no latency. For example, after imaging tasks have been completed, the object may be moved to a treatment position, and the control transfer may be performed seamlessly without any delay. In some embodiments, the control transfer may occur while the table is moving between an imaging position and a treatment position.

Specifically, in the present disclosure, systems and methods for controlling movement of a table supporting an object shared between multiple devices are provided. An exemplary system may include a first control sub-system operably coupled to a first device and a second control sub-system operably coupled to a second device. The first control sub-system may generate a first control instruction. The second control sub-system may generate a second control instruction. The system may further include a master controller (also referred to as the virtual master node mentioned above) configured to receive the first control instruction from the first control sub-system, or the second control instruction from the second control sub-system. The master controller may further generate a third control instruction based on the first control instruction or the second control instruction. The master controller may transmit the third control instruction to a table control sub-system. The table control sub-system may be operably coupled to the table. The table control sub-system may generate a control signal based on the third control instruction, and cause the table to move based on the control signal. In some embodiments, the master controller and the table control sub-system may be integrated into a table controller.

Figure 5:
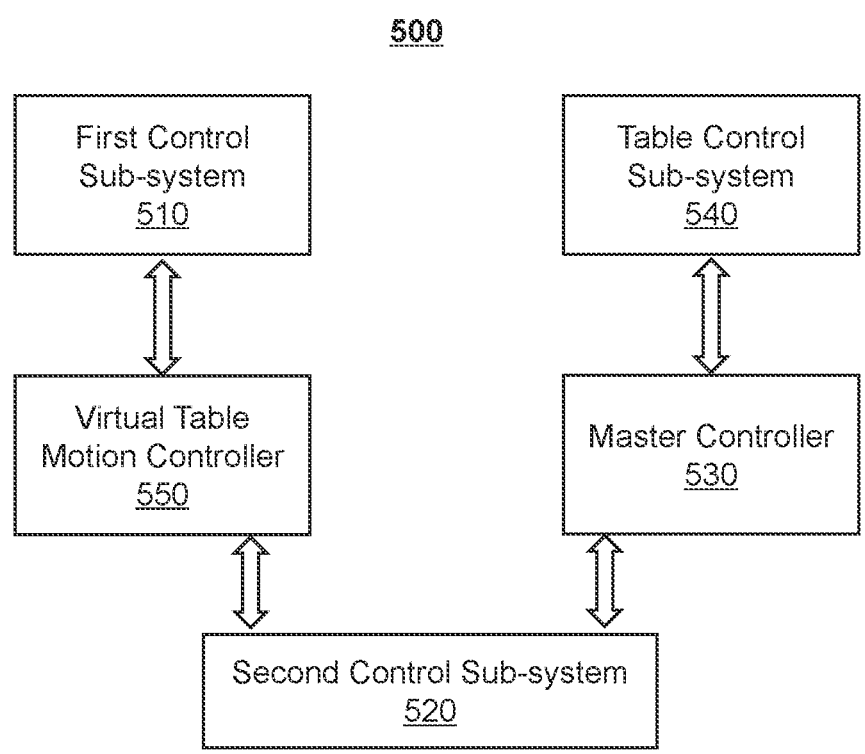
FIG. 5 is a block diagram illustrating a first exemplary system of the medical apparatus according to some embodiments of the present disclosure.
Figure 7:
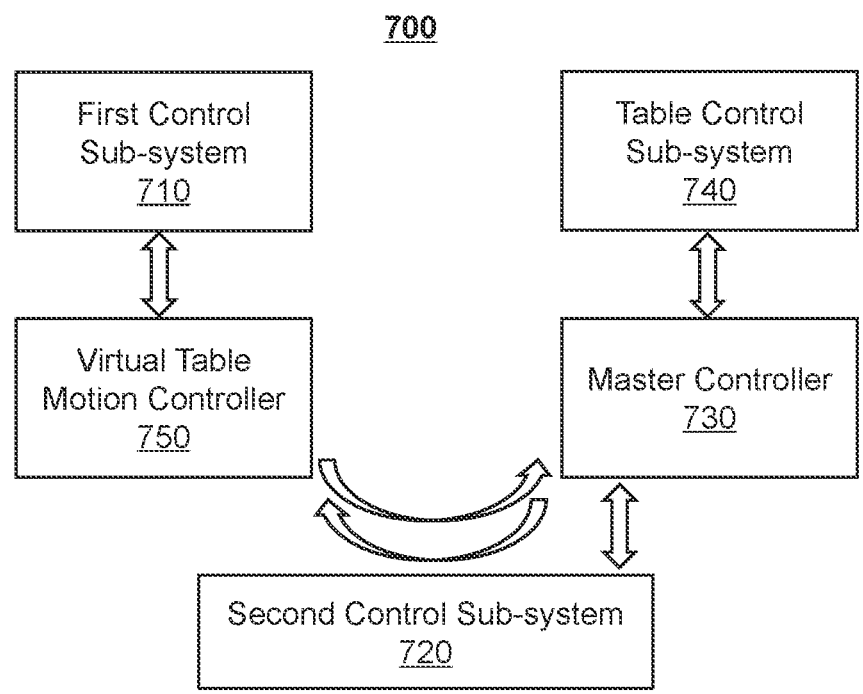
FIG. 7 is a block diagram illustrating a second exemplary system of the medical apparatus according to some embodiments of the present disclosure.

According to the present disclosure, the shared table implementation is provided with minor modifications to the RT control system (or RT controller) and no modifications to the CT control system (or CT controller). Therefore, an imaging system (of any modality such as CT, MRI, PET-CT, etc.) can be easily integrated into another system (e.g., an RT system), with virtually no changes to the control system of the imaging system. In some cases (e.g., with a smart switch), no modifications may be made even to the RT control system. This allows the RT control system to optionally be integrated with the imaging system or to work as a stand-alone configuration with virtually no changes to the control system implementation. In some embodiments, as illustrated in FIG. 5, the RT control system can monitor all communication to the table and therefore is aware that whether the CT control system is controlling the table. In some embodiments, as illustrated in FIG. 7, in a smart switch implementation, the integration (of the RT system and the imaging system) can be hidden from the RT control system. Therefore, both the RT system and the imaging system can be developed independently, and the integration can be simplified.

It should be noted that although the following descriptions are describing the shared table control between an RT device and a CT device, the descriptions are merely provided for the purposes of illustration, and not intended to limit the scope of the present disclosure. Systems and methods according to some embodiments of the present disclosure may be extended to shared table control between other systems, for example, another imaging and therapy apparatus that may be collocated in a same treatment room and share a same table (e.g., an MR-RT apparatus, or a positron emission tomography (PET)/CT-RT apparatus, or the like), an imaging system and treatment apparatus (e.g., a CT device combined with an X-ray inspection device capable of angiographic inspection). As another example, systems and methods according to some embodiments of the present disclosure may be applied to the control of a component shared by multiple devices.

Figure 1:
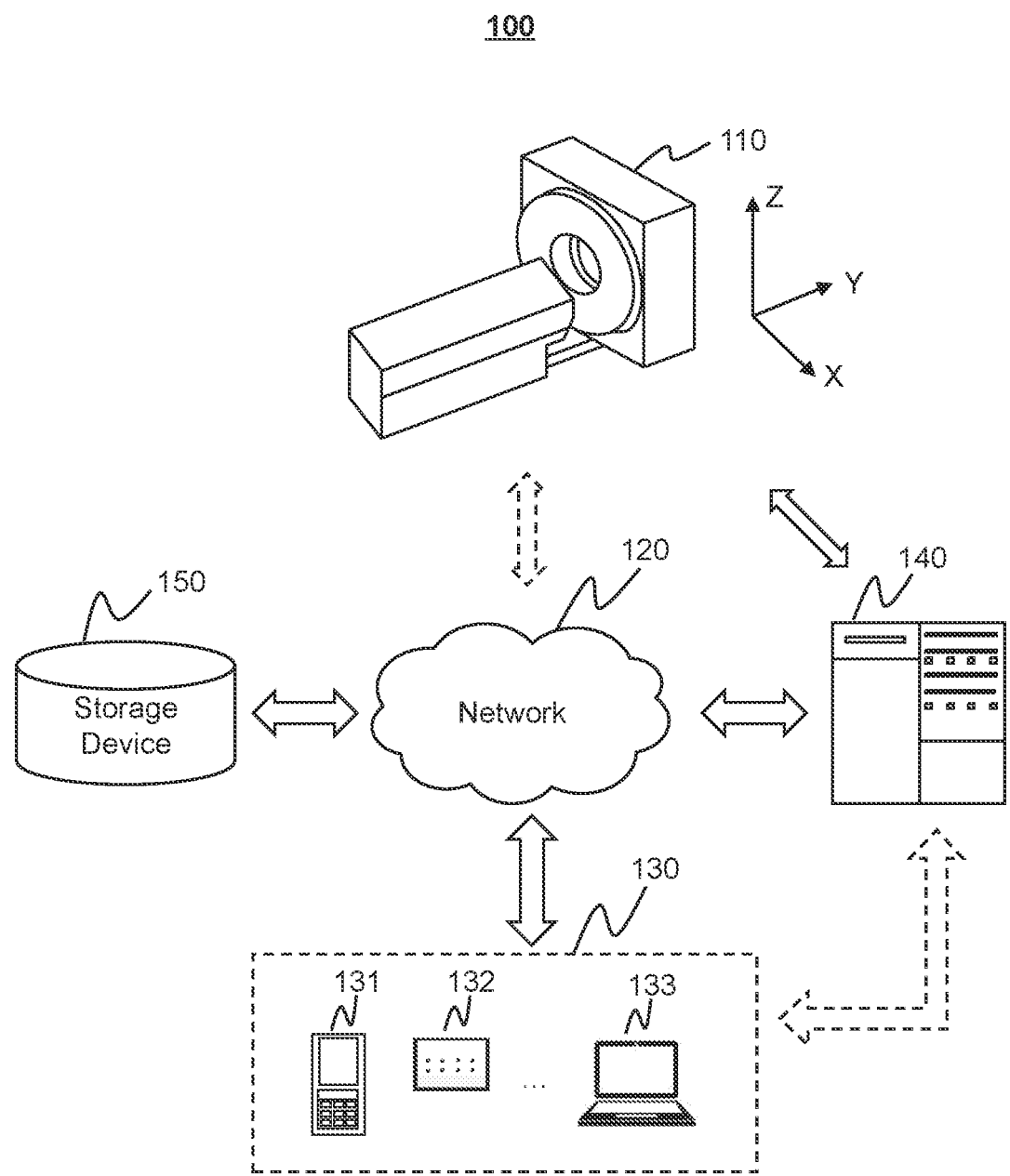
FIG. 1 is a schematic diagram illustrating an exemplary radiation system according to some embodiments of the present disclosure.

FIG. 1 is a schematic diagram illustrating an exemplary radiation system according to some embodiments of the present disclosure. As shown in FIG. 1, the radiation system 100 may include a medical apparatus 110, a network 120, one or more terminals 130, one or more processing devices 140, and one or more storage devices 150. The components in the radiation system 100 may be connected in one or more of various ways. Merely by way of example, the medical apparatus 110 may be connected to the one or more processing devices 140 directly (e.g., via optical fiber (e.g., a peripheral component interconnect express (PCI-E) cable)). As another example, the medical apparatus 110 may be connected to the one or more processing devices 140 through the network 120 as indicated by the bi-directional arrow in dotted lines linking the medical apparatus 110 and the network 120. As still another example, the storage device(s) 150 may be connected to the one or more processing devices 140 directly or through the network 120. As still another example, the terminal(s) 130 may be connected to the one or more processing devices 140 directly (as indicated by the bi-directional arrow in dotted lines linking the terminal(s) 130 and the one or more processing devices 140) or through the network 120.

The medical apparatus 110 may include one or more imaging devices, one or more treatment devices, a table shared by the imaging device(s) and/or the treatment device(s), or the like. In some embodiments, the medical apparatus 110 may include an imaging device of a first modality, an imaging device of a second modality, a table shared by the two imaging devices, or the like. The first modality may be different from the second modality. For example, the imaging device of the first modality may be a computed tomography (CT) imaging device, while the imaging device of the second modality may be a magnetic resonance imaging (MRI) imaging device. In some embodiments, the medical apparatus 110 may include an imaging device (e.g., a CT device) combined or integrated with a treatment device (e.g., an RT device).

The imaging device may be configured to generate image data of an object (e.g., a patient). Exemplary imaging devices may include a CT device, a magnetic resonance imaging (MRI) device, a single photon emission computed tomography (SPECT) device, a positron emission tomography (PET) device, a PET-CT device, or the like, or any combination thereof. For illustration purpose, the imaging device is described as a CT device herein, and the description thereof is not intended to limit the scope of the present disclosure. The imaging device may include an imaging radiation source, a detector, a gantry, or the like. The imaging radiation source and the detector may be mounted on the gantry. The imaging radiation source may emit radiation rays (e.g., X-ray) to the object (e.g., a patient) placed on the table. The detector may detect at least a portion of the radiation rays traversing the object. In some embodiments, the detector may include one or more detector units. The one or more detector units may include a scintillation detector (e.g., a cesium iodide detector, a gadolinium oxysulfide detector). The detector may include a single-row detector and/or a multi-rows detector.

In some embodiments, the imaging device may transmit the image data (e.g., directly or via the network 120) to the one or more processing devices 140, the storage device(s) 150, and/or the terminal device(s) 130 for further processing. For example, the image data may be sent to the one or more processing devices 140 for generating an image of the object, or may be stored in the storage device(s) 150. The image of the object may be used to determine and/or track the location of a treatment region of the object. In some embodiments, the treatment region may refer to the region that needs to be irradiated. In some embodiments, the treatment region may be a portion of the object, for example, a head, a breast, a lung, an abdomen, a large intestine, a small intestine, a bladder, a gallbladder, a pancreas, a prostate, a uterus, an ovary, a liver, or the like, or a portion thereof, or any combination thereof. In the present disclosure, "object" and "subject" are used interchangeably. In some embodiments, the treatment region may include an abnormal tissue, for example, a tumor, a polyp, or the like.

The treatment device may be configured to deliver one or more treatment beams (e.g., radiation rays) to the treatment region (e.g., a tumor). The radiation rays may be delivered toward the treatment region for radiation therapy based on the determined or tracked location of the treatment region. The radiation ray used herein may include a particle ray, a photon ray, etc. The particle ray may include neutron, proton, electron, u-meson, heavy ion, a-ray, or the like, or any combination thereof. The photon ray may include X-ray, y-ray, ultraviolet, laser, or the like, or any combination thereof. For illustration purposes, a treatment device associated with X-ray may be described as an example. In some embodiments, the medical apparatus 110 may generate a prescribed dose of X-rays to perform radiotherapy based on the image data provided by the imaging device. For example, the image data may be processed to locate a tumor and/or determine the dose of X-rays.

The treatment device may include a treatment radiation source, a gantry, and a collimator. In some embodiments, the treatment radiation source may include a linear accelerator (LINAC) that accelerates electrons and generates radiation rays thereby. In some embodiments, the collimator may delimit the shape of the radiation rays and/or generate prescribed treatment beams according to a treatment plan.

The medical apparatus 110 may have various configurations. In some embodiments, the imaging device may be spaced by a distance from the treatment device. In some embodiments, the gantry of the imaging device and the gantry of the treatment device may share a same axis of rotation. In some embodiments, the imaging device and the treatment device may share a same gantry. In some embodiments, the object may remain at a same position on the table for imaging and treatment. In some embodiments, the table may be caused to move to different positions for imaging and treatment. More descriptions of the configurations of the medical apparatus 110 may be found elsewhere in the present disclosure (e.g., FIGS. 4A-4D and descriptions thereof). In some embodiments, the imaging device may be operably coupled to a first processing device, while the treatment device may be operably coupled to a second processing device. In some embodiments, the imaging device and the treatment device may be operably coupled to a single processing device.

The table may include a tabletop and a base frame. In some embodiments, the tabletop may move along a longitudinal axis direction and enter into a bore of the gantry of the imaging device and/or the treatment device. In some embodiments, the tabletop may move two-dimensionally, three-dimensionally, four-dimensionally, five-dimensionally, or six-dimensionally. In some embodiments, the position of the tabletop may be adjusted according to a variation (e.g., a position change) of a target volume (e.g., a tumor) of the object estimated by, for example, a real-time image obtained by the imaging device during a treatment process. In the present disclosure, moving the tabletop of a table may be described as moving the table for brevity. As used herein, the term "table" may refer to a movable portion, e.g., a movable tabletop, of a table for brevity.

The network 120 may include any suitable network that can facilitate exchange of information and/or data for the radiation system 100. In some embodiments, one or more components of the radiation system 100 (e.g., the medical apparatus 110, the terminal(s) 130, the one or more processing devices 140, the storage device(s) 150, etc.) may communicate information and/or data with one or more other components of the radiation system 100 via the network 120. For example, the one or more processing devices 140 may obtain data related to the motion information of the table from the medical apparatus 110 via the network 120. As another example, the one or more processing devices 140 may obtain user instructions from the terminal(s) 130 via the network 120. The network 120 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network ("VPN"), a satellite network, a telephone network, routers, hubs, switches, server computers, and/or any combination thereof. Merely by way of example, the network 120 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 120 may include one or more network access points. For example, the network 120 may include wired and/or wireless network access points such as base stations and/or internet exchange points through which one or more components of the radiation system 100 may be connected to the network 120 to exchange data and/or information.

Figure 3:
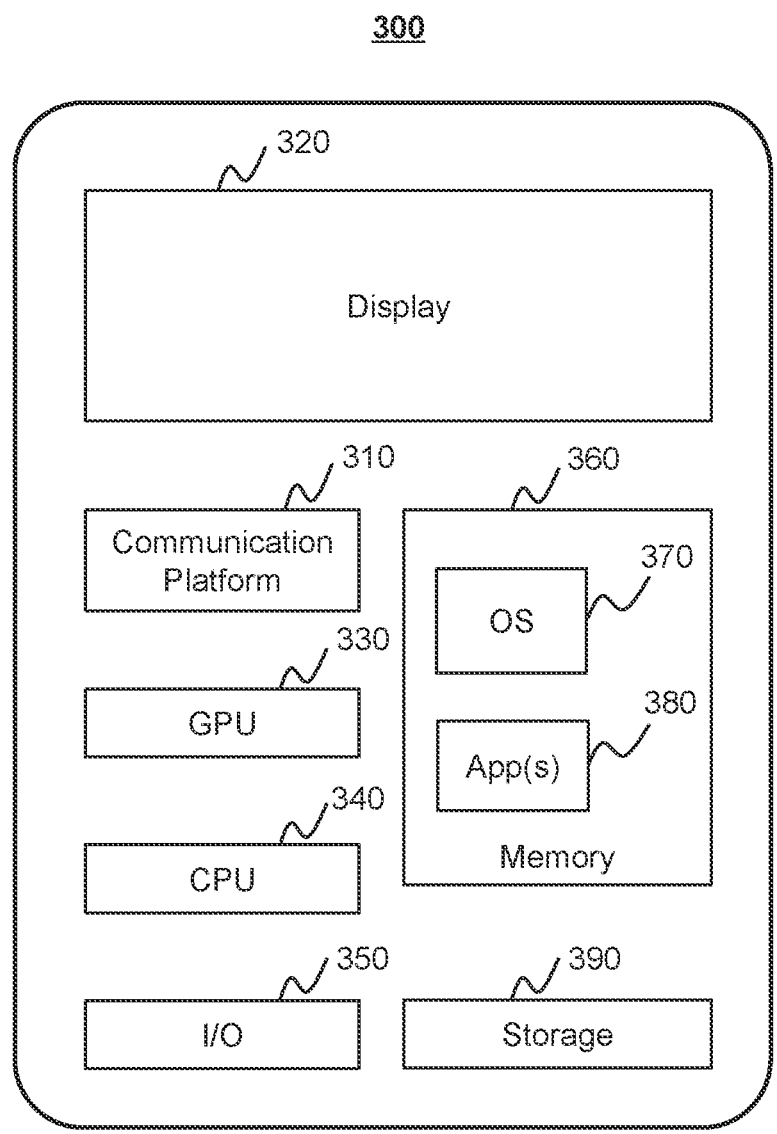
FIG. 3 is a schematic diagram illustrating exemplary hardware and/or software components of an exemplary mobile device on which the terminal may be implemented according to some embodiments of the present disclosure.

The terminal(s) 130 may enable interactions between a user and the radiation system 100. The terminal(s) 130 may include a mobile device 131, a tablet computer 132, a laptop computer 133, or the like, or any combination thereof. In some embodiments, the mobile device 131 may include a smart home device, a wearable device, a mobile device, a virtual reality device, an augmented reality device, or the like, or any combination thereof. Merely by way of example, the terminal(s) 130 may include a mobile device as illustrated in FIG. 3. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a bracelet, a footgear, eyeglasses, a helmet, a watch, clothing, a backpack, a smart accessory, or the like, or any combination thereof. In some embodiments, the mobile device may include a mobile phone, a personal digital assistant (PDA), a gaming device, a navigation device, a point of sale (POS) device, a laptop, a tablet computer, a desktop, or the like, or any combination thereof. In some embodiments, the virtual reality device and/or the augmented reality device may include a virtual reality helmet, virtual reality glasses, a virtual reality patch, an augmented reality helmet, augmented reality glasses, an augmented reality patch, or the like, or any combination thereof. For example, the virtual reality device and/or the augmented reality device may include a Google Glass™, an Oculus Rift™, a Hololens™, a Gear VR™, etc. In some embodiments, the terminal(s) 130 may be part of the one or more processing devices 140. In some embodiments, the terminal(s) 130 may remotely operate the medical apparatus 110. In some embodiments, the terminal(s) 130 may operate the medical apparatus 110 via a wireless connection. In some embodiments, the terminal(s) 130 may receive information and/or instructions inputted by a user, and send the received information and/or instructions to the medical apparatus 110 or the one or more processing devices 140 via the network 120. In some embodiments, the terminal(s) 130 may receive data and/or information from the one or more processing devices 140. In some embodiments, the terminal(s) 130 may be omitted.

The one or more processing devices 140 may process data and/or information obtained from the medical apparatus 110, the terminal(s) 130, and/or the storage device(s) 150. For example, the one or more processing devices 140 may process image data and reconstruct one or more images based on the image data. As another example, the one or more processing devices 140 may determine the position of the treatment region based on the one or more images. The image(s) may be used to detect a position of a target volume (e.g., a tumor) and/or detect whether a shape and/or size of the tumor has changed in comparison with a treatment plan. If the shape and/or size of the tumor has changed, the treatment plan may be modified to adapt to the current conditions of the tumor.

In some embodiments, the one or more processing devices 140 may be a single processing device that communicates with and/or process data from the imaging device and the treatment device of the medical apparatus 110. Alternatively, the one or more processing devices 140 may include at least two processing devices. One of the at least two processing devices may communicate with and/or process data from the imaging device of the medical apparatus 110, and another one of the at least two processing devices may communicate with and/or process data from the treatment device of the medical apparatus 110. In some embodiments, the at least two processing devices may communicate with each other. In some embodiments, the one or more processing devices 140 may include a first control sub-system (associated with the imaging device) configured to generate a first control instruction. In some embodiments, the one or more processing devices 140 may include a second control sub-system (associated with the treatment device) configured to generate a second control instruction. The first control instruction and/or the second control instruction may be configured to control the movement of the table. In the present disclosure, a control sub-system is also referred to as a controller. For example, the first control sub-system is also referred to as a first controller, and a second control sub-system is also referred to as a second controller. In some embodiments, the first controller and/or the second controller may be part of the terminal(s) 130.

In some embodiments, the one or more processing devices 140 may be a computer, a user console, a single server or a server group, etc. The server group may be centralized or distributed. In some embodiments, the one or more processing devices 140 may be local or remote. For example, the one or more processing devices 140 may access information and/or data stored in the medical apparatus 110, the terminal(s) 130, and/or the storage device(s) 150 via the network 120. As another example, one or more processing devices 140 may be directly connected to the medical apparatus 110, the terminal(s) 130, and/or the storage device(s) 150 to access stored information and/or data. In some embodiments, one or more processing devices 140 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, one or more processing devices 140 may be implemented by a computing device 200 having one or more components as illustrated in FIG. 2. In some embodiments, one or more processing devices 140 may be part of the terminal(s) 130. In some embodiments, one or more processing devices 140 may be devices independent from the terminal(s) 130 and can communicate with the terminal(s) 130.

In some embodiments, the medical apparatus 110 may further include a master controller. The master controller may be configured to control movement of the table supporting the object according to control commands from the imaging device and/or the treatment device. For example, the master controller may receive the first control instruction from the first controller, or the second control instruction from the second controller. As another example, the master controller may generate a third control instruction based on the first control instruction or the second control instruction. As a further example, the master controller may transmit the third control instruction to a table controller (also referred to as a table control sub-system). The table controller may be configured to generate a control signal based on the third control instruction and/or cause the table to move based on the control signal. In some embodiments, the master controller may be part of the processing device(s) 140. More descriptions of the master controller may be found elsewhere in the present disclosure (e.g., FIGS. 5-8 and descriptions thereof).

In some embodiments, the medical apparatus 110 may further include a table controller operably coupled to the table. The table controller may include at least one processor in communication with the imaging device and/or the treatment device. The table controller may be configured to control movement of the table of the medical apparatus 110 according to control commands from the imaging device and/or the treatment device. For example, the table controller may receive a first control instruction from the imaging device via a first interface. As another example, the table controller may receive a second control instruction from the treatment device via a second interface. As still another example, the table controller may generate a control signal based on the first control instruction and/or the second control instruction; and/or cause the table to move based on the control signal. More descriptions of the table controller may be found elsewhere in the present disclosure (e.g., FIGS. 5-10 and descriptions thereof).

In some embodiments, components of the radiation system 100 (e.g., the medical apparatus 110, the terminal(s) 130, the one or more processing devices 140) may communicate with each other in a radiation treatment process. For example, before the radiation treatment process starts, the terminal(s) 130 may send instruction(s) or information related to a movement of the table to the one or more processing devices 140. The one or more processing devices 140 may determine preset parameters (e.g., preset positions, preset velocities, and/or preset accelerations) based on the instruction(s) or information related to the movement, and/or store the preset parameters (e.g., in the storage device(s) 150). As another example, before the radiation treatment process starts, the preset parameters may be determined by the terminal(s) 130, and/or stored in the terminal(s) 130. Alternatively, the terminal(s) 130 may transmit the preset parameters to the one or more processing devices 140, and the preset parameters may be stored in the one or more processing devices 140. As still another example, during the radiation treatment process, the one or more processing devices 140 may obtain the preset parameters from the terminal(s) 130. As a further example, during the radiation treatment process, the medical apparatus 110 may transmit a current status (e.g., a current position, and/or a current velocity) of the table to the one or more processing devices 140, and the one or more processing devices 140 may drive the table to move based on the preset parameters, and/or the current status of the table. As still a further example, the one or more processing devices 140 may transmit the current status of the table to the terminal(s) 130 for display.

The storage device(s) 150 may store data, instructions, and/or any other information. In some embodiments, the storage device(s) 150 may store data obtained from the medical apparatus 110, the terminal(s) 130, and/or the one or more processing devices 140. For example, the storage device(s) 150 may store a treatment plan, information related to a motion control of the table (e.g., information related to control commands of the table), information related to motion statuses of the table (e.g., a velocity, an acceleration, a target position, a current position, etc.), or the like. In some embodiments, the storage device(s) 150 may store data and/or instructions that the one or more processing devices 140 (or any controller in the present disclosure) may execute or use to perform exemplary methods described in the present disclosure. In some embodiments, the storage device(s) 150 may include a mass storage device, a removable storage device, a volatile read-and-write memory, a read-only memory (ROM), or the like, or any combination thereof. Exemplary mass storage devices may include a magnetic disk, an optical disk, a solid-state drive, etc. Exemplary removable storage devices may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device(s) 150 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device(s) 150 may be connected to the network 120 to communicate with one or more other components in the radiation system 100 (e.g., the one or more processing devices 140, the terminal(s) 130, etc.). One or more components in the radiation system 100 may access the data or instructions stored in the storage device(s) 150 via the network 120. In some embodiments, the storage device(s) 150 may be directly connected to or communicate with one or more other components in the radiation system 100 (e.g., the one or more processing devices 140, the terminal(s) 130, etc.). In some embodiments, the storage device(s) 150 may be part of the one or more processing devices 140. In some embodiments, the one or more processing devices 140 may be connected to or communicate with the medical apparatus 110 via the network 120, or at the backend of the one or more processing devices 140.

FIG. 2 is a schematic diagram illustrating exemplary hardware and/or software components of an exemplary computing device on which the one or more processing devices 140 may be implemented according to some embodiments of the present disclosure. As illustrated in FIG. 2, the computing device 200 may include a processor 210, a storage 220, an input/output (I/O) 230, and a communication port 240.

The processor 210 may execute computer instructions (e.g., program code) and perform functions of the one or more processing devices 140 in accordance with techniques described herein. The computer instructions may include, for example, routines, programs, objects, components, data structures, procedures, modules, and functions, which perform particular functions described herein. For example, the processor 210 may process data obtained from the medical apparatus 110, the terminal(s) 130, the storage device(s) 150, and/or any other component of the radiation system 100. In some embodiments, the processor 210 may determine preset position(s) of the table based on information relating to a treatment plan. The treatment plan may be obtained from a treatment planning system (TPS) associated with the radiation system 100. The information relating to the treatment plan may include preoperative medical image(s) representing the internal anatomical information of an object to be treated or imaged. In some embodiments, the processor 210 may perform motion control of the table based on the treatment plan. In some embodiments, the processor 210 may determine an imaging protocol for imaging the object. In some embodiments, the processor 210 may perform motion control of the table based on the imaging protocol. In some embodiments, the processor 210 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 200. However, it should be noted that the computing device 200 in the present disclosure may also include multiple processors, thus operations and/or method steps that are performed by one processor as described in the present disclosure may also be jointly or separately performed by the multiple processors. For example, if in the present disclosure the processor of the computing device 200 executes both operation A and operation B, it should be understood that operation A and operation B may also be performed by two or more different processors jointly or separately in the computing device 200 (e.g., a first processor executes operation A and a second processor executes operation B, or the first and second processors jointly execute operations A and B).

The storage 220 may store data/information obtained from the medical apparatus 110, the terminal(s) 130, the storage device(s) 150, and/or any other component of the radiation system 100. In some embodiments, the storage 220 may include a mass storage device, a removable storage device, a volatile read-and-write memory, a read-only memory (ROM), or the like, or any combination thereof. For example, the mass storage device may include a magnetic disk, an optical disk, a solid-state drive, etc. The removable storage may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage 220 may store one or more programs and/or instructions to perform exemplary methods described in the present disclosure. For example, the storage 220 may store a program for controlling the table to move.

The I/O 230 may input and/or output signals, data, information, etc. In some embodiments, the I/O 230 may enable a user interaction with the one or more processing devices 140. In some embodiments, the I/O 230 may include an input device and an output device. Examples of the input device may include a keyboard, a mouse, a touch screen, a microphone, or the like, or a combination thereof. Examples of the output device may include a display device, a loudspeaker, a printer, a projector, or the like, or a combination thereof. Examples of the display device may include a liquid crystal display (LCD), a light-emitting diode (LED)-based display, a flat panel display, a curved screen, a television device, a cathode ray tube (CRT), a touch screen, or the like, or a combination thereof.

The communication port 240 may be connected to a network (e.g., the network 120) to facilitate data communications. The communication port 240 may establish connections between the one or more processing devices 140 and the medical apparatus 110, the terminal(s) 130, and/or the storage device(s) 150. The connection may be a wired connection, a wireless connection, any other communication connection that can enable data transmission and/or reception, and/or any combination of these connections. The wired connection may include, for example, an electrical cable, an optical cable, a telephone wire, or the like, or any combination thereof. The wireless connection may include, for example, a Bluetooth™ link, a Wi-Fi™ link, a WiMax™ link, a WLAN link, a ZigBee link, a mobile network link (e.g., 3G, 4G, 5G, etc.), or the like, or a combination thereof. In some embodiments, the communication port 240 may be and/or include a standardized communication port, such as RS232, RS485, etc. In some embodiments, the communication port 240 may be a specially designed communication port. For example, the communication port 240 may be designed in accordance with the digital imaging and communications in medicine (DICOM) protocol.

FIG. 3 is a schematic diagram illustrating exemplary hardware and/or software components of an exemplary mobile device on which the terminal(s) 130 may be implemented according to some embodiments of the present disclosure. As illustrated in FIG. 3, the mobile device 300 may include a communication platform 310, a display 320, a graphics processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300. In some embodiments, a mobile operating system 370 (e.g., iOS™, Android™, Windows Phone™, etc.) and one or more applications 380 may be loaded into the memory 360 from the storage 390 in order to be executed by the CPU 340. The applications 380 may include a browser or any other suitable mobile apps for receiving and rendering information relating to image processing or other information from the one or more processing devices 140. User interactions with the information stream may be achieved via the I/O 350 and provided to the one or more processing devices 140 and/or other components of the radiation system 100 via the network 120. In some embodiments, a user may input parameters to the radiation system 100, via the mobile device 300.

In order to implement various modules, units and their functions described above, a computer hardware platform may be used as hardware platforms of one or more elements (e.g., the one or more processing devices 140 and/or other components of the radiation system 100 described in FIG. 1). Since these hardware elements, operating systems and program languages are common; it may be assumed that persons skilled in the art may be familiar with these techniques and they may be able to provide information needed in the imaging according to the techniques described in the present disclosure. A computer with the user interface may be used as a personal computer (PC), or other types of workstations or terminal devices. After being properly programmed, a computer with the user interface may be used as a server. It may be considered that those skilled in the art may also be familiar with such structures, programs, or general operations of this type of computing device.

FIGS. 4A-4D are schematic diagrams illustrating exemplary configurations of the medical apparatus 110 according to some embodiments of the present disclosure. The table shown in FIGS. 4A-4D is shared by a first device (e.g., an imaging device) and a second device (e.g., a treatment device). Merely by way of example, the imaging device may be a CT imaging device (e.g., a megavoltage CT (MVCT), a kilovoltage CT (KVCT), a cone-beam CT (CBCT), a CT on rail, etc.).

Figure 4A:
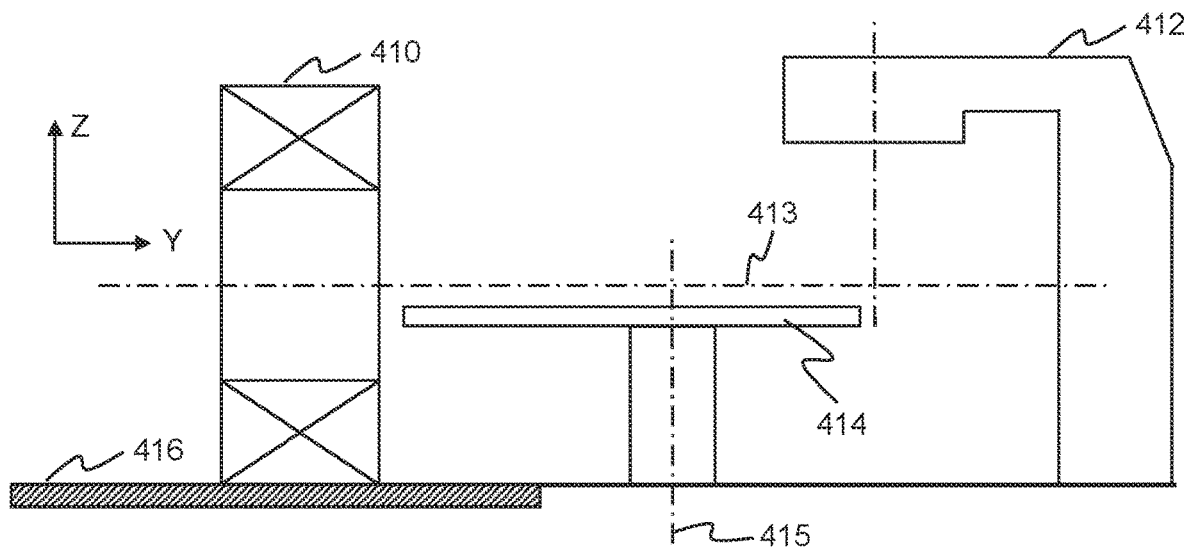
FIGS. 4A-4D are schematic diagrams illustrating exemplary configurations of the medical apparatus 110 according to some embodiments of the present disclosure.

FIG. 4A illustrates an exemplary imaging-treatment apparatus. As shown in FIG. 4A, the imaging-treatment apparatus 400A may include an imaging device 410 (e.g., a CT imaging device), a treatment device 412, and a table 414. The imaging device 410 may generate image data of an object (e.g., a patient) positioned on the table 414. The imaging device 410 may provide the image data of the object before, during, and/or after at least a portion of a radiation therapy is performed on the object. More descriptions regarding the imaging device 410 may be found elsewhere in the present disclosure (e.g., FIG. 1, and the descriptions thereof). The treatment device 412 may perform radiation therapy on the object positioned on the table 414. More descriptions regarding the treatment device 412 may be found elsewhere in the present disclosure (e.g., FIG. 1, and the descriptions thereof). The table 414 may support the object for imaging using the imaging device 410 and/or radiation therapy using the treatment device 412.

As illustrated in FIG. 4A, the imaging device 410 and the treatment device 412 may be spaced apart, and the table 414 may be located between the treatment device 412 and the imaging device 410. The table 414 may be moveable along a longitudinal direction 413 of the table 414. For example, a tabletop of the table 414 may be moveable relative to the treatment device 412. The moving range of the tabletop of the table 414 may extend to a treatment position. The treatment position may refer to a position where the object can receive radiation beams delivered from the treatment device 412. In some embodiments, the table 414 may be rotatable around a vertical rotation axis 415. In some embodiments, the imaging device 410 may be moveable relative to the table 414 (or the treatment device 412). In some embodiments, the imaging device 410 may be placed on a rail 416 so that the imaging device 410 may move along the rail 416 (e.g., CT on rail). The gantry of the imaging device 410 may be moveable back and forth along the rail 416. In some embodiments, the rail 416 may extend along the longitudinal direction of the table 414. If the object needs to be imaged, the imaging device 410 may move along the rail 416 relative to the table 414 to reach an imaging position. The imaging position may refer to a position where the object can be imaged. In the imaging position, a bore of the gantry of the imaging device 410 may embrace at least a portion of the table 414 and at least a portion of the object thereon. In some embodiments, if the object on the table 414 is to be imaged, the table 414 may not need to be synchronized with the imaging device 410 (e.g., the table 414 may only be controlled by the treatment device 412 and may be left stationary when the imaging device 410 is working or preparing for working), and the imaging device 410 may move along the rail 416 to reach the imaging position so that image data of the object may be generated by the imaging device 410 (e.g., in order to assess whether the target volume has a variance with respect to the treatment plan before the treatment process starts).

In some embodiments, a controller of the imaging device 410 may control the longitudinal motion of the imaging device 410 on the rail 416. In some embodiments, after the imaging is finished, the imaging device 410 may move away from the table 414. Alternatively or additionally, in some embodiments, if the object on the table 414 is to be imaged, the table 414 may be synchronized with the imaging device 410. For example, when the imaging device 410 reaches a certain position (e.g., a position with a predetermined distance away from the treatment device 412), the imaging device 410 may not need to be moved, and the table 414 may be moved (e.g., under the control of the imaging device 410) towards the imaging device 410. In some embodiments, the synchronization between the table 414 and the imaging device 410 may be realized using the systems illustrated in FIGS. 5-10. In some embodiments, there may be an angle between an extension direction of the rail 416 and the longitudinal direction of the table 414. In order for the object or the table 414 to align with the imaging device 410, the table 414 may rotate by an angle around the rotation axis 415, and then the imaging device 410 may move along the rail 416 to reach the imaging position.

Figure 4B:
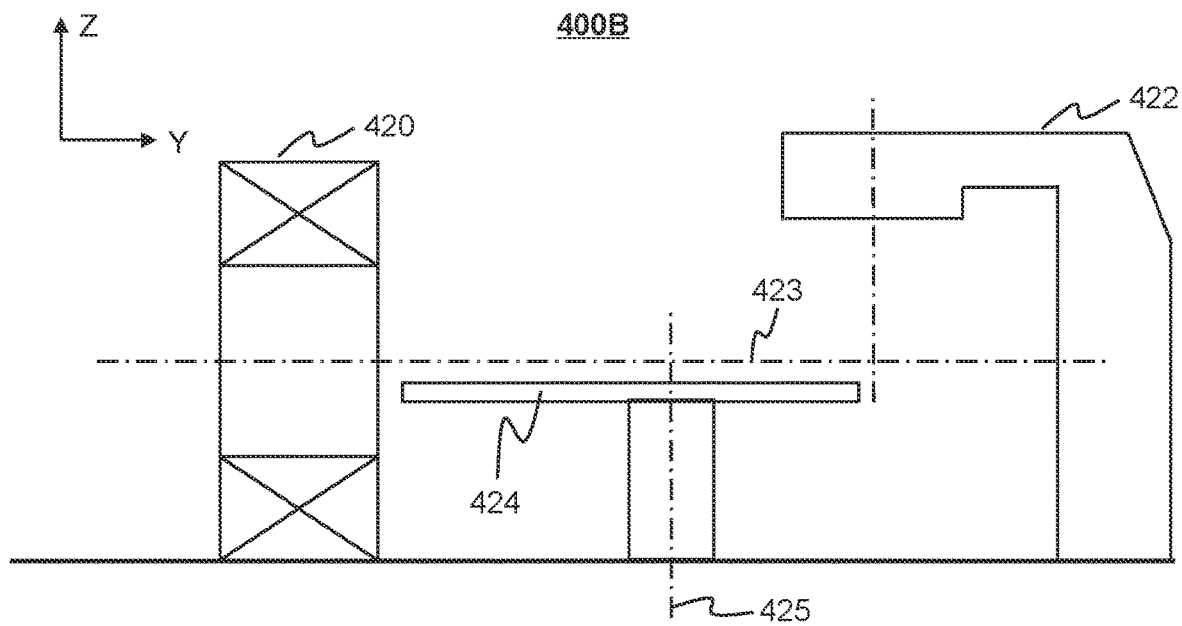

FIG. 4B illustrates another exemplary imaging-treatment apparatus. As shown in FIG. 4B, the imaging-treatment apparatus 400B may include an imaging device 420 (e.g., a CT imaging device), a treatment device 422, and a table 424. The imaging device 420 may generate image data of an object (e.g., a patient) positioned on the table 424. The imaging device 420 may provide the image data of the object before, during, and/or after at least a portion of a radiation therapy is performed on the object. Unlike the imaging device 410 in FIG. 4A, there may be no rail to guide the imaging device 420 to move, and the imaging device 420 may have a fixed position. More descriptions regarding the imaging device 420 may be found elsewhere in the present disclosure (e.g., FIG. 1, and the descriptions thereof). The treatment device 422 may perform radiation therapy on the object positioned on the table 424. More descriptions regarding the treatment device 422 may be found elsewhere in the present disclosure (e.g., FIG. 1, and the descriptions thereof). As illustrated in FIG. 4B, the imaging device 420 and the treatment device 422 may be spaced apart, and the table 424 may be located between the treatment device 422 and the imaging device 420. The table 424 may support the object for imaging using the imaging device 420 and/or radiation therapy using the treatment device 422. The table 424 may be moveable along a longitudinal direction 423 of the table 424. The table 424 may be moveable back and forth between the treatment device 422 and the imaging device 420. The moving range of the table 424 may extend to the treatment position of the treatment device 422. The moving range of the table 424 may extend to the imaging position of the imaging device 420. If the object needs to be treated, the table 424 may be moved to the treatment position. If the object needs to be imaged, the table 424 may be moved to the imaging position. In some embodiments, in order for the object or the table 424 to align with the imaging device 420, the table 424 may rotate by an angle around the rotation axis 425 to facilitate the imaging process.

Figure 4C:
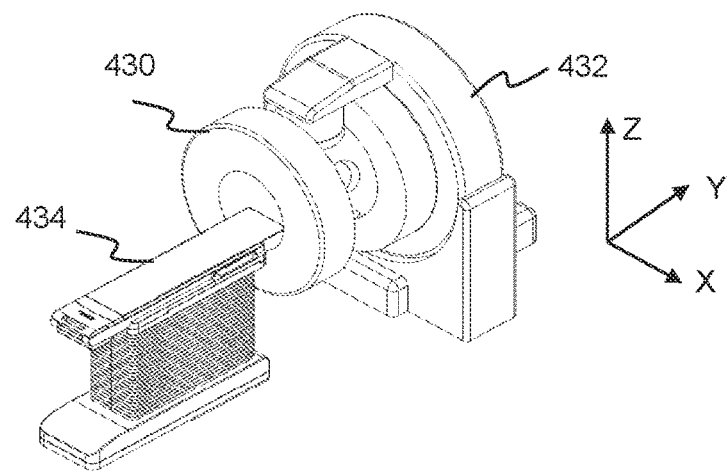

FIG. 4C illustrates another exemplary imaging-treatment apparatus. As shown in FIG. 4C, the imaging-treatment apparatus 400C may include an imaging device 430 (e.g., a CT imaging device), a treatment device 432, and a table 434. The imaging device 430 may generate image data of an object (e.g., a patient) on the table 434. The imaging device 430 may provide the image data of the object before, during, and/or after at least a portion of a radiation therapy is performed on the object. More descriptions regarding the imaging device 430 may be found elsewhere in the present disclosure (e.g., FIG. 1, and the descriptions thereof). The treatment device 432 may perform radiation therapy on the object positioned on the table 434. More descriptions regarding the treatment device 432 may be found elsewhere in the present disclosure (e.g., FIG. 1, and the descriptions thereof). As illustrated in FIG. 4C, the imaging device 430 may be located between the treatment device 432 and the table 434 (i.e., the imaging device 430 may be located in front of the treatment device 432 (from the table's point of view)). The table 434 may support the object for imaging using the imaging device 430 and/or radiation therapy using the treatment device 432. The table 434 may be moveable back and forth along a longitudinal direction (e.g., the Y-axis direction) of the table 434. The longitudinal direction of the table 434 may be parallel to an axial direction of a bore of the treatment device 432 and/or a bore of the imaging device 430. If the object needs to be treated, the table 434 carrying the object may be moved to the treatment position. If the object needs to be imaged, the table 434 carrying the object may be moved to the imaging position.

Figure 4D:
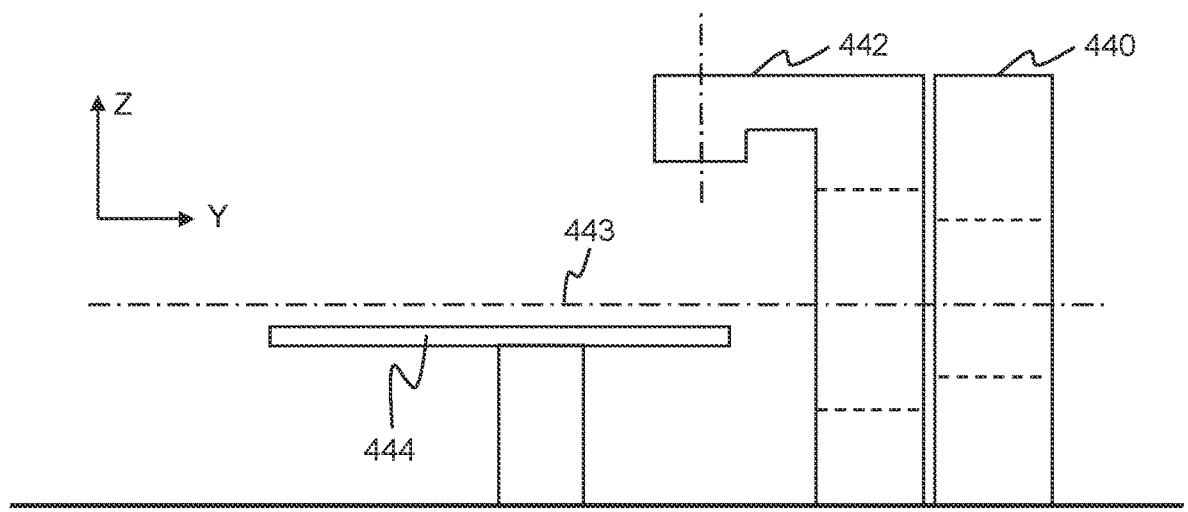

FIG. 4D illustrates another exemplary imaging-treatment apparatus. As shown in FIG. 4D, the imaging-treatment apparatus 400D may include an imaging device 440 (e.g., a CT imaging device), a treatment device 442, and a table 444. The functions of the imaging device 440 and the treatment device 442 may be similar to the imaging devices 430 and the treatment device 432, respectively. As illustrated in FIG. 4D, the treatment device 442 may be located between the imaging device 440 and the table 444 (i.e., the imaging device 430 may be located behind the treatment device 432 (from the table's point of view)). The table 444 may support the object for imaging using the imaging device 440 and/or radiation therapy using the treatment device 442. The table 444 may be moveable back and forth along a longitudinal direction 443 of the table 444. At least a portion of the table 444 may move through a bore of the treatment device 442 and/or a bore of the imaging device 440. If the object needs to be treated, the table 444 may be moved to the treatment position. If the object needs to be imaged, the table 444 may be moved to the imaging position.

The imaging devices 410, 420, 430, and 440 and the treatment devices 412, 422, 432, and 442 are merely provided for the purposes of illustration, and not intended to limit the scope of the present disclosure. Systems and methods according to some embodiments of the present disclosure may be extended to the control of a component shared by multiple devices, e.g., a shared table control between systems other than those described in connection with FIGS. 4A-4D, for example, another imaging and therapy apparatus that may be collocated in a same treatment room and share a same table (e.g., an MR-RT apparatus, or a positron emission tomography (PET)/CT-RT apparatus, or the like), an imaging system and treatment apparatus (e.g., a CT device combined with an X-ray inspection device capable of angiographic inspection).

FIG. 5 is a block diagram illustrating a first exemplary system of the medical apparatus 110 according to some embodiments of the present disclosure. As illustrated in FIG. 5, the system 500 may be part of the one or more processing devices 140. The system 500 may control the movement of a table of the medical apparatus 110. In some embodiments, similar to FIGS. 4A-4D, the table may be shared by a first device (e.g., an imaging device) and a second device (e.g., a treatment device). The system 500 may include a first control sub-system 510 associated with the first device, a second control sub-system 520 associated with the second device, a master controller 530, and a table control sub-system 540.

In some embodiments, the second device may be associated with the second control sub-system 520, the master controller 530, and the table control sub-system 540. In some embodiments, the table control sub-system 540 may be operably coupled to the table. The master controller 530 may be operably connected to the table control sub-system 540. For example, the master controller 530 may be connected to the table control sub-system 540 via an electrical cable, and the communication between the master controller 530 and the table control sub-system 540 may be performed based on a controller area network (CAN) protocol. The CAN protocol may be a robust bus standard designed to allow controllers (e.g., the table control sub-system 540, the master controller 530) and/or devices thereof to communicate with each other in applications without a host computer. The second control sub-system 520 may be operably connected to the master controller 530. For example, the second control sub-system 520 may be connected to the master controller 530 via a peripheral component interconnect express (PCIE) cable, and the communication between the second control sub-system 520 and the master controller 530 may be performed based on a PCIE protocol. The PCIE protocol may be an interface standard for connecting high-speed components (e.g., the second control sub-system 520, the master controller 530) and/or realizing high-speed communication between the components. In some embodiments, the second control sub-system 520 may be part of the terminal 130. In some embodiments, the second control sub-system 520 may be part of the processing device 140.

The second control sub-system 520 may be configured to control the second device to perform one or more functionalities (e.g., beam on/off, radiation dose control, gantry angle adjustment, and/or aperture shape formation of a collimator in radiation treatment of the object) and control the movement of the table to cause one or more desired functionalities to be performed on the object. In some embodiments, the second control sub-system 520 may generate one or more control commands (also referred to as control instructions) to control the movement of the table.

In some embodiments, the master controller 530 may be configured to relay the control commands from the second control sub-system 520 to the table control sub-system 540 to control the movement of the table. The master controller 530 may function as a relay station. In some embodiments, the master controller 530 may be further configured to relay information relating to table statuses received from the table control sub-system 540 to the second control sub-system 520.

The table control sub-system 540 may be configured to directly control the movement of the table. In some embodiments, the table control sub-system 540 may control the movement of the table and adjust the position of the table in real time. In some embodiments, the table control sub-system 540 may control the table to move to a plurality of positions in one or more directions (e.g., the X-axis direction, the Y-axis direction, and/or the Z-axis direction illustrated in FIGS. 1 and 4A-4D). The movements in the one or more directions may be referred to as axial movements (e.g., an X-axial movement, a Y-axial movement, and/or a Z-axial movement). In some embodiments, the table control sub-system 540 may control the table to rotate around one or more axes (e.g., a first rotation axis parallel to the Y-axis, and/or a second rotation axis parallel to the Z-axis) of the table. A rotation around the one or more axes may be referred to as a rotational movement. In some embodiments, the table control sub-system 540 may include one or more sub-controllers. A sub-controller may be configured to control a specific movement (e.g., an axial movement in a direction, a rotational movement around a rotation axis). For example, the table control sub-system 540 may include a first sub-controller controlling the axial movements and a second sub-controller controlling the rotational movements. As another example, the table control sub-system 540 may include three sub-controllers, each of which controlling a movement in a certain direction (e.g., the X-axis direction, the Y-axis direction, and/or the Z-axis direction). In some embodiments, the table control sub-system 540 may include a single integrated controller configured to control the different movements (e.g., the axial movements and the rotational movements). In some embodiments, the table control sub-system 540 may further include a driving circuit configured to generate, based on the control signals generated by the table control sub-system 540, a driving force to drive the table to move.

The second control sub-system 520 may control the movement of the table when the second device is in its working condition. To control the movement of the table, the second control sub-system 520 may generate one or more second table packets and transmit the second table packet(s) to the master controller 530. The second table packet(s) may include one or more second control instructions, second time information associated with the second control sub-system 520, a source (e.g., the second control sub-system 520) IP address, a destination (e.g., the master controller 530, the table control sub-system 540) IP address, a sequence number (or sequence identification (ID)) of the second table packet, routing information, etc. The second control instruction(s) may be generated based on or include a second prescribed motion profile of the table. A motion profile may refer to a profile describing a trajectory of the table (e.g., movements and/or positions of the table at different time points). The second motion profile may include a start time point of a motion, an acceleration of a motion, a velocity of a motion, a deceleration of a motion, a target position of the table, or the like, or any combination thereof. In some embodiments, the second prescribed motion profile may be generated by the second control sub-system 520 before a radiation delivery starts or at the beginning of the radiation delivery. In some embodiments, the second prescribed motion profile may be determined based on a treatment plan associated with the radiation delivery.

The second time information may include second clock synchronization information, representing the clock of the second device (e.g., a timestamp for an event occurred in or relating to the second device). In some embodiments, the second time information may be used to assess whether the clock of the table control sub-system 540 (and/or the master controller 530) is synchronized with the clock of the second control sub-system 520. In some embodiments, if the clock of the table control sub-system 540 (and/or the master controller 530) is not synchronized with the clock of the second control sub-system 520, the second time information may be used to synchronize the clock of the table control sub-system 540 (and/or the master controller 530) with the clock of the second control sub-system 520. In the present disclosure, that a first clock of a first sub-system (e.g., the master controller 530, the table control sub-system 540) is not synchronized with a second clock of a second sub-system (e.g., the second control sub-system 520) may refer to a situation that the difference between the first clock and the second clock is greater than a clock threshold. The clock threshold may be determined by the radiation system 100, or may be preset by a user or operator via the terminal(s) 130.

In some embodiments, upon receiving the (second) table packet(s), the master controller 530 may parse the (second) table packet(s), and/or transmit a portion or all of the information (e.g., the second control instruction(s), the second time information) in the (second) table packet(s) to the table control sub-system 540. In some embodiments, the master controller 530 may assess, based on the second time information, whether the clock of the master controller 530 is synchronized with the clock of the second control sub-system 520. In some embodiments, if the clock of the master controller 530 is not synchronized with the clock of the second control sub-system 520, the master controller 530 may synchronize, based on the second time information, the clock of the master controller 530 with the clock of the second control sub-system 520. In some embodiments, if the clock of the master controller 530 is not synchronized with the clock of the second control sub-system 520, the master controller 530 may report the desynchrony status (or the time information of the master controller 530) to the second control sub-system 520.

In some embodiments, upon receiving the information transmitted from the master controller 530, the table control sub-system 540 may generate one or more control signals based on the received information (e.g., the second control instruction(s)) and cause the table to move based on the control signal(s) so that the table can move according to the second prescribed motion profile. In some embodiments, the table control sub-system 540 may assess, based on the received information (e.g., the second time information), whether the clock of the table control sub-system 540 is synchronized with the clock of the second control sub-system 520. In some embodiments, if the clock of the table control sub-system 540 is not synchronized with the clock of the second control sub-system 520, the table control sub-system 540 may synchronize, based on the second time information, the clock of the table control sub-system 540 with the clock of the second control sub-system 520. In some embodiments, if the clock of the table control sub-system 540 is not synchronized with the clock of the second control sub-system 520, the table control sub-system 540 may report the desynchrony status (or the time information of the table control sub-system 540) to the second control sub-system 520 via the master controller 530.

In some embodiments, the table control sub-system 540 may detect motion statuses of the table and transmit information relating to the motion statuses to the master controller 530. The information relating to the motion statuses of the table may include a position of the table, a moving direction of the table, a moving distance of the table, a trajectory of the table, a velocity of the table, an acceleration of the table, an angular velocity of the table, a locked/unlocked status of the table, a motion enabled status of the table, a fault flag (if any), or the like, or any combination thereof. In a locked status, the table may be forced to stop and remain immobile until further instructions are given. If any fault occurs, the table may be in the locked status, and/or a fault flag may be generated. The motion enable state of the table may indicate which control sub-system is in control of the movement of the table. The fault flag may indicate whether a fault is detected, when the fault is detected, and/or what fault is detected. In some embodiments, the table control sub-system 540 may transmit the time information of the table control sub-system 540 or clock synchronization information (e.g., whether the clock of the table control sub-system 540 is synchronized) to the master controller 530. In some embodiments, the master controller 530 may transmit the information received from the table control sub-system 540 to the second control sub-system 520. In some embodiments, the master controller 530 may transmit clock synchronization information (e.g., whether the clock of the master controller 530 is synchronized) to the second control sub-system 520. In some embodiments, upon receiving information transmitted from the master controller 530, the second control sub-system 520 may assess whether an actual motion profile (or a portion thereof (e.g., an actual trajectory)) of the table is in accordance with the prescribed motion profile (or a portion thereof (e.g., the prescribed trajectory)). If the actual motion profile deviates by more than a specified tolerance from the prescribed motion profile, the actual motion profile of the table may be determined to deviate from the prescribed motion profile of the table. The tolerance may be determined by the radiation system 100, or may be preset by a user or operator via the terminal(s) 130, or may be adjustable under different situations. For example, the tolerance may be relatively small if the motion profile is generated by the second control sub-system 520, because the Y-axial movement or position of the table needs to be coordinated with a treatment plan with a relatively high accuracy. As another example, the tolerance may be relatively small if the motion profile is generated by the first control sub-system 510, because the Y-axial movement of the table needs to be coordinated with a gantry (e.g., a CT gantry) motion with a relatively high accuracy for image capture and image reconstruction. In response to a determination that the actual motion profile of the table deviates from the prescribed motion profile of the table, the table may be locked by the second control sub-system 520 (when the second control sub-system 520 is controlling the table), and thus the table may be in the locked status.

In some embodiments, upon receiving information transmitted from the master controller 530, the second control sub-system 520 may determine whether the clock of the master controller 530 and/or the table control sub-system 540 is synchronized with the clock of the second control sub-system 520. In response to a determination that the clock of the master controller 530 and/or the table control sub-system 540 is not synchronized with the clock of the second control sub-system 520, a fault flag may be generated. Further, the second control sub-system 520 may synchronize the clock of the master controller 530 and/or the table control sub-system 540 with the clock of the second control sub-system 520. Alternatively, the second control sub-system 520 may transmit its own time information to the master controller 530 and/or the table control sub-system 540 to make the master controller 530 and/or the table control sub-system 540 to synchronize their clocks with the second control sub-system 520.

In some embodiments, the first device may be directly integrated into or operably connected to the second device, and the first control sub-system 510 of the first device may communication with the table control sub-system 540 via the master controller 530. In some embodiments, the first control sub-system 510 may be part of (or coupled to) the first device. In some embodiments, the first control sub-system 510 may be part of the terminal 130. In some embodiments, the first control sub-system 510 may be part of the processing device 140. The first control sub-system 510 may be configured to control the first device to perform one or more functionalities (e.g., gantry rotation, imaging of an object) and control the movement of the table to cause one or more desired functionalities to be performed on the object.

In some embodiments, the first control sub-system 510 associated with the first device may be operably coupled to the second device (e.g., the second control sub-system 520 and/or the master controller 530 associated with the second device) so that the first control sub-system 510 and the master controller 530 have a point-to-point connection. An exemplary point-to point connection may include a peripheral component interconnect express (PCIE) connection. For example, the first control sub-system 510 may be operably connected to a PCIE card in the second device so that the first control sub-system 510 is operably coupled to the second control sub-system 520 and/or the master controller 530 associated with the second device. In some embodiments, the second device may include one or more peripheral component interconnect express (PCIE) slots to mount one or more PCIE cards. The PCIE slots may have various physical configurations: x1, x4, x8, x16, x32. The number after the letter "x" may indicate a count of lanes (indicating how much data travels to and from a PCIE card) that a PCIE slot has. For example, a PCIE x1 slot may have one lane and may transmit data at one bit per cycle, while a PCIE x2 slot may have two lanes and may transmit data at two bits per cycle. In some embodiments, the PCIE slots may be set in a mainboard of the second control sub-system 520, and thus the PCIE card can be mounted on the mainboard of the second control sub-system 520. As illustrated above, an operable connection between the first device and the second device may be realized using the PCIE card. In some embodiments, with the point-to-point connection, information transmitted from the first control sub-system 510 may travel through the PCIE card of the second control sub-system 520 and directly to the master controller 530. Accordingly, information transmitted from the master controller 530 may travel through the PCIE card and directly to the first control sub-system 510. The communication between the first control sub-system 510 and the master controller 530 via the second control sub-system 520 may be performed based on a PCIE protocol.

In some embodiments, the first control sub-system 510 may communicate (via one or more relay stations (e.g., the virtual table motion controller 550 and/or the master controller 530)) with the table control sub-system 540 through a CAN or CANOpen protocol. In some embodiments, the virtual table motion controller 550 may be configured to tunnel the CAN or CANOpen protocol into a PCIE packet (also referred to a first table packet) to adapt to the point-to-point connection (between the first control sub-system 510 and the master controller 530) on the basis of the PCIE protocol. The virtual table motion controller 550 may function as a relay station. In some embodiments, the virtual table motion controller 550 may send the PCIE packet to the second control sub-system 520. In some embodiments, the second control sub-system 520 may decode the PCIE packet and send the decoded PCIE packet to the master controller 530. In some embodiments, the master controller 530 may convert the (decoded) PCIE packet back into the CAN or CANOpen protocol, and send the packet to the table control sub-system 540, and then the table control sub-system 540 may control the table based on the instruction(s) from the first control sub-system 510. In some embodiments of the present disclosure, although the first control sub-system 510 is connected to the mainboard of the second control sub-system 520, a CPU of the mainboard of the second control sub-system 520 may be bypassed in the information transmission between the first control sub-system 510 and the master controller 530, and the first control sub-system 510 and the master controller 530 may be communicated through the point-to-point connection directly. Using the point-to-point connection, the communication between the first control sub-system 510 and the master controller 530 may be performed efficiently with low latency. For example, a latency time between the master controller 530 and the first control sub-system 510 may be less than 10 microseconds. In the configuration of the system 500, the virtual table motion controller 550 and the master controller 530 may function as relay stations that convert the communication protocol of the first control sub-system 510 to minimize the latency, the cabling, etc. With the point-to-point connection and the low latency thereof, the first control sub-system 510 may control the movement of the table via the master controller 530.

In some embodiments, if the first device is in its working condition, the first control sub-system 510 may control the movement of the table. To control the movement of the table, the first control sub-system 510 may generate one or more first table packets and transmit the first table packet(s) to the table control sub-system 540 via one or more relay stations (e.g., the virtual table motion controller 550, the master controller 530). The first table packet(s) may include one or more first control instructions, first time information associated with the first control sub-system 510, a source (e.g., the first control sub-system 510) IP address, a destination (e.g., the master controller 530, the table control sub-system 540) IP address, a sequence number (or sequence identification (ID)) of the first table packet, routing information, etc. The first control instruction(s) may be generated based on or include a first prescribed motion profile of the table. The first prescribed motion profile may include a velocity of the table at a specific time point, an acceleration of the table at a specific time point, a target position of the table at a specific time point, etc. The first prescribed motion profile of the table may be different from the second prescribed motion profile of the table. The first prescribed motion profile may be generated and/or updated by the first control sub-system 510 before image acquisition starts or at the beginning of the image acquisition of the object. In some embodiments, the first prescribed motion profile may be generated based on a (CT) scan protocol for the image acquisition. A scan protocol may include a detector configuration, a tube current, a tube potential, a reconstruction algorithm, an object positioning, a scan range, a reconstructed slice thickness, etc.

The first time information may include first clock synchronization information, representing the clock of the first device (e.g., a timestamp for an event occurred in or relating to the first device). In some embodiments, the first time information may be used to assess whether the clock of the table control sub-system 540 (and/or the master controller 530) is synchronized with the clock of the first control sub-system 510. In some embodiments, if the clock of the table control sub-system 540 (and/or the master controller 530) is not synchronized with the clock of the first control sub-system 510, the first time information may be used to synchronize the clock of the table control sub-system 540 (and/or the master controller 530) with the clock of the first control sub-system 510.

If the first control sub-system 510 is controlling the table, the communication between the master controller 530 and the table control sub-system 540, the clock synchronization of the master controller 530 and/or the table control sub-system 540, and/or the functionalities of the master controller 530 and/or the table control sub-system 540 on the basis of the first table packet(s) may be similar to that described above when the second control sub-system 520 is controlling the table. In some embodiments, the first control sub-system 510 may receive information relating to the motion statuses of the table from the table control sub-system 540 via one or more relay stations (e.g., the master controller 530 and/or the virtual table motion controller 550). For example, the master controller 530 may relay the information relating to the motion statuses of the table from the table control sub-system 540 to the virtual table motion controller 550 via the second control sub-system 520, and the virtual table motion controller 550 may relay the information to the first control sub-system 510. In some embodiments, the first control sub-system 510 may assess whether an actual motion profile (or a portion thereof (e.g., an actual trajectory)) of the table is in accordance with the prescribed motion profile (or a portion thereof (e.g., the prescribed trajectory)) of the table. In response to a determination that the actual motion profile of the table deviates from the prescribed motion profile of the table, the table may be locked by the first control sub-system 510 (when the first control sub-system 510 is controlling the table), and thus the table may be in the locked status. In some embodiments, upon receiving information transmitted from the master controller 530, the first control sub-system 510 may determine whether the clock of the master controller 530 and/or the table control sub-system 540 is synchronized with the clock of the first control sub-system 510. In response to a determination that the clock of the master controller 530 and/or the table control sub-system 540 deviates from the clock of the first control sub-system 510, a fault flag may be generated. Further, the first control sub-system 510 may synchronize the clock of the master controller 530 and/or the table control sub-system 540 with the clock of the first control sub-system 510. Alternatively, the first control sub-system 510 may transmit its own time information to the master controller 530 and/or the table control sub-system 540 to make the master controller 530 and/or the table control sub-system 540 to synchronize their clocks with the first control sub-system 510.

From the point of view of the first control sub-system 510, the first control sub-system 510 is directly connected to a table motion controller, and the first control sub-system 510 can control the movement of the table by transmitting corresponding control commands to the table motion controller (via one or more relay stations). With the relay stations (e.g., the virtual table motion controller 550 and/or the master controller 530), the first control sub-system 510 may act as if it communicates directly with the table control sub-system 540, while actually, the first control sub-system 510 may communicate with the table control sub-system 540 via the virtual table motion controller 550, the second control sub-system 520, and the master controller 530 as described above. In some embodiments, the virtual table motion controller 550 may be regarded as a portion of the second control sub-system 520 or a portion of the master controller 530.

In some embodiments, the master controller 530 may relay first control instruction(s) from the first control sub-system 510 or second control instruction(s) from the second control sub-system 520 to the table control sub-system 540. In some embodiments, the master controller 530 may function as a relay station. In some embodiments, the master controller 530 may further function as a real controller. For example, the master controller 530 may synchronize and/or control the flow of control from commands sent by the first control sub-system 510 and the second control sub-system 520.

In some embodiments, the master controller 530 may generate one or more third control instructions based on the first control instruction(s) or the second control instruction(s). In some embodiments, the master controller 530 may transmit the third control instruction(s) to the table control sub-system 540. The third control instruction(s) may be generated based on the first control instruction(s) or the second control instruction(s). For example, upon receiving the first control instruction(s) or the second control instruction(s), the master controller 530 may generate the third control instruction(s) by adjusting the first control instruction(s) or the second control instruction(s) according to the communication protocol (e.g., a CAN protocol) between the master controller 530 and the table control sub-system 540. In some embodiments, the table control sub-system 540 may control the movement of the table based on the third control instruction(s). For example, the table may be caused to move according to a control signal that is generated, based on the third control instruction(s), by the table control sub-system 540.

In some embodiments, the master controller 530 may update the time information associated with the master controller 530 according to a received table packet (e.g., the first table packet, the second table packet) to synchronize the clock of the master controller 530 with the clock of the first control sub-system 510 (if the first control sub-system 510 in controlling the table) or the clock of the second control sub-system 520 (if the second control sub-system 520 is controlling the table). If the master controller 530 receives the first control instruction(s) (e.g., when the first device controls the movement of the table), the time information of the master controller 530 may be updated according to the first clock synchronization information in the first table packet. If the master controller 530 receives the second control instruction(s) (e.g., when the second device controls the movement of the table), the time information of the master controller 530 may be updated according to the second clock synchronization information in the second table packet.

In some embodiments, upon receiving information relating to statuses of the table from the table control sub-system 540, the master controller 530 may transmit the information to the second control sub-system 520. In some embodiments, upon receiving the information, the second control sub-system 520 may determine whether the table is under a control of the first control sub-system 510. In response to a determination that the table is under the control of the first control sub-system 510, the second control sub-system 520 may cause the information relating to the table statuses to be transmitted from the master controller 530 to the first control sub-system 510 via the point-to-point connection therebetween.

In some embodiments, at least a portion of the system 500 (e.g., the first control sub-system 510, the second control sub-system 520, the master controller 530, and/or the table control sub-system 540) may know or be informed of which device (e.g., the first control sub-system 510 associated with the first device, or the second control sub-system 520 associated with the second device) is controlling the table based on the table packet(s) (e.g., the first table packet(s), the second table packet(s)) transmitted to the master controller 530 or the table control sub-system 540. For example, the source IP address included in the table packet(s) may indicate which device is controlling the table. As another example, the table packet(s) may further include label information indicating which device is controlling the table.

In some embodiments, at least a portion of the system 500 may know or be informed of which device is controlling the table by determining which device of the medical apparatus 110 (either the first device or the second device) is in its working condition. For example, if the first time information in two or more first table packets is updated continuously, it may be determined that the first device is in its working condition, and is controlling the table. As another example, if the second time information in two or more second table packets is updated continuously, it may be determined that the second device is in its working condition, and is controlling the table.

In some embodiments, at least a portion of the system 500 may know or be informed of which device is controlling the table based on a workflow of the system 500. In some embodiments, the workflow may include two phases, e.g., an image acquisition phase and a radiation treatment delivery phase. If the workflow proceeds to the image acquisition phase, the first control sub-system 510 may control the table. If the workflow proceeds to the radiation treatment delivery phase, the second control sub-system 520 may control the table. In some embodiments, the workflow may be managed by a user (e.g., a radiologist, a therapist). For example, if the workflow proceeds to the image acquisition phase, the user may cause the table to move to an imaging position. Once the table reaches the imaging position, the first control sub-system 510 may start to control the table, or the user may cause the first control sub-system 510 to start to control the table. As another example, if the workflow proceeds to the radiation treatment delivery phase, the user may cause the table to move to a treatment position. Once the table reaches the treatment position, the second control sub-system 520 may start to control the table, or the user may cause the second control sub-system 520 to start to control the table. In some embodiments, the workflow may be automatically managed by the system 500 (e.g., a preselected workflow that runs on the second control sub-system 520) For example, if the workflow proceeds to the image acquisition phase, the second control sub-system 520 may transfer the control of the table to the first control sub-system 510, so that the first control sub-system 510 can control the table. If image acquisition is finished and the workflow proceeds to the radiation treatment delivery phase, the second control sub-system 520 may control the table. In some embodiments, the first control sub-system 510 may inform the master controller 530 and/or the second control sub-system 520, and then the master controller 530 may cause the table to move to the treatment position.

In some embodiments, if the first control sub-system 510 is ready to or needs to control the table, the first control sub-system 510 may determine whether the table is under control of the second control sub-system 520. In some embodiments, if the first control sub-system 510 finishes its intended functionalities (e.g., imaging the object), the first control sub-system 510, the master controller 530, and/or the table control sub-system 540 may transmit a notification to the second control sub-system 520. In some embodiments, if the second control sub-system 520 finishes its intended functionalities (e.g., radiation treatment of the object), the second control sub-system 520, the master controller 530, and/or the table control sub-system 540 may transmit a notification to the first control sub-system 510. In some embodiments, the control of the table may be granted to only one of the first control sub-system 510 and the second control sub-system 520, and thus no conflict may occur.

According to the configuration of the system 500, the first control sub-system 510 and the second control sub-system 520 may be kept fairly independent, and the control of the table may be transparent for them. There is no need to modify the control system of the imaging device (e.g., the first control sub-system 510) to enable it to have access and control of the table. Using the configuration of the system 500, the coupling of the control systems of the imaging device and the treatment device can be simplified. Besides, the imaging device and the treatment device can be developed independently without much interdependencies.

As illustrated in FIG. 5, the performance of the functionalities of the first device (or the second device) may depend on the clock synchronization between the first control sub-system 510 (or the second control sub-system 520) and the table control sub-system 540. In some embodiments, the clock synchronization may be performed during a system initialization process (e.g., at the start of a day). Table packet(s) from the first control sub-system 510 may be relayed to the table control sub-system 540 (e.g., via the virtual table motion controller 550 and/or the master controller 530). During this time, the second control sub-system 520 may be in a stand-by state, and/or at least a portion of the second control sub-system 520 may relay the table packet(s) from the first control sub-system 510 to the table control sub-system 540 (e.g., via the master controller 530). The first control sub-system 510 may rely on the clock synchronization to delegate the control (e.g., the motion profile control) of the table to the table control sub-system 540 when the first control sub-system 510 controls the gantry motion so that both the table control and the gantry control are coordinated using the synchronized clock. Once the image acquisition is completed, the first control sub-system 510 may surrender the control of the table to the second control sub-system 520. In some embodiments, generated images may be sent from the first control sub-system 510 to the second control sub-system 520 for processing and/or display.

In some embodiments, latency may need to be minimized to maintain the synchronization of the clock of the components of the system 500. By using the point-to-point connection, the latency may be relatively low or low enough to maintain the clock synchronization. In some embodiments, the coordination of the first device and the second device can be realized by synchronizing the clocks of all relevant components (e.g., the first control sub-system 510 (or the second control sub-system 520), the master controller 530, the virtual table motion controller 550) and by transmitting the prescribed motion profile (either the first prescribed motion profile or the second prescribed motion profile) to an end controller (e.g., the table control sub-system 540). The end controller may be informed of when table motion needs to be started according to the prescribed motion profile. Because the clocks are synchronized, the end controller can independently start the table motion and follow the prescribed motion profile at correct time points. The first device (and/or the second device) can be synchronized with the motion profile of the table, since they share the same clock. Because the motion profile is prescribed, the clocks of the components of the system 500 are synchronized, and the first control sub-system 510 (or the second control sub-system 520) know where the table needs to be according to the motion profile, there may be no need to have a very precise low latency trigger. Besides, information relating to table statuses may be provided to the first control sub-system 510 (or the second control sub-system 520) with time information (e.g., a timestamp for an event occurred in or relating to the table) so that the first control sub-system 510 (or the second control sub-system 520) can assess an actual motion profile from the table control sub-system 540 with respect to the prescribed motion profile.

Using this mechanism illustrated in FIG. 5, a high speed bus may be omitted from the system 500, since what is critical is the synchronization of the clocks of the components of the system 500, which may be achieved without such a high speed bus. The motion profiles of the table may be pre-defined, and the controllers of the first device and/or the second device can independently follow the pre-defined motion profiles. In addition, no significant modification of currently available first device and/or second device is needed. The fast communication between components within the system 500 may be achieved by utilizing a PCIE card with the PCIE protocol, without incurring additional cost.

It should be noted that the above description of the system 500 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, the second device may be integrated into the first device.

Figure 6:
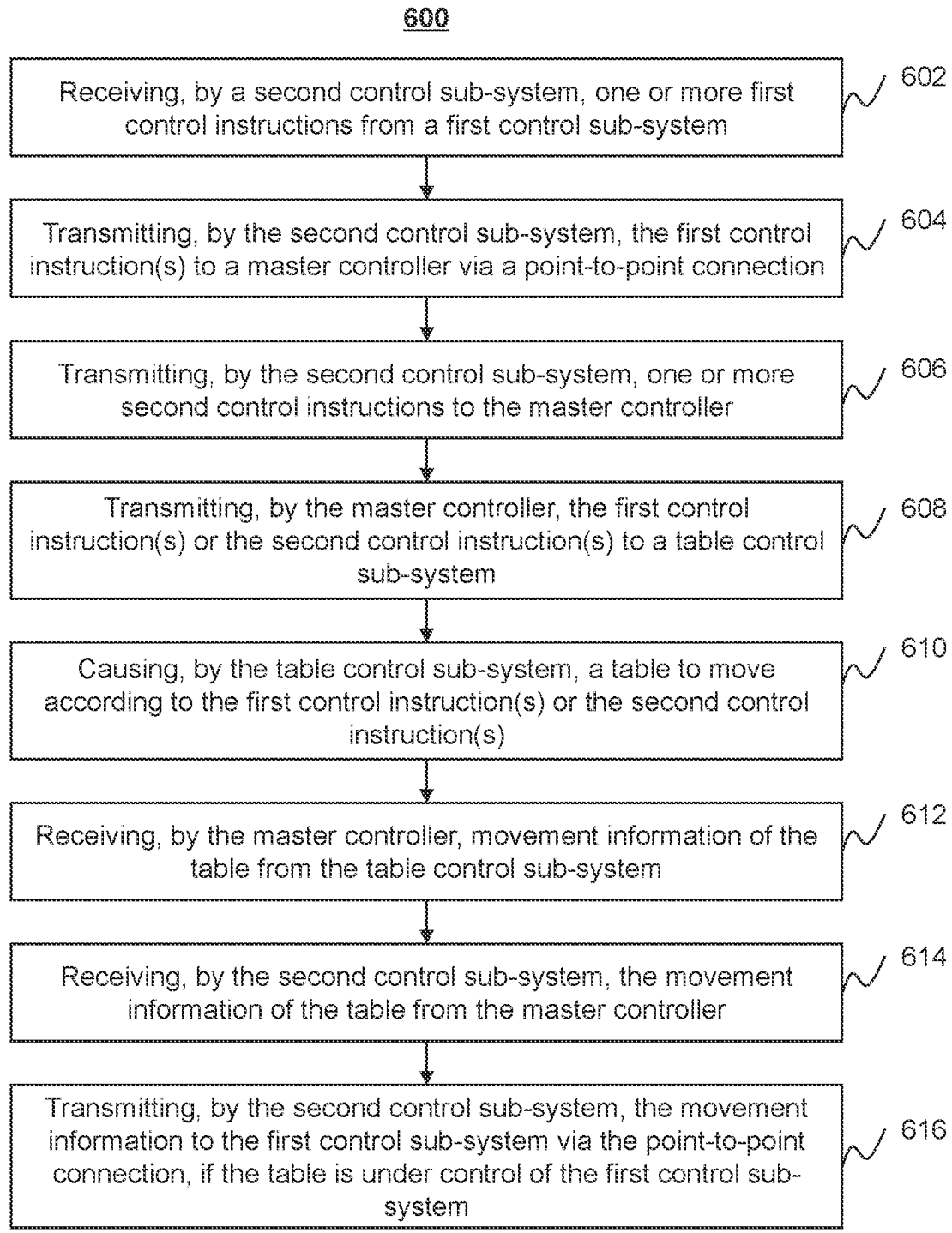
FIG. 6 is a flowchart illustrating an exemplary process for controlling movement of a table according to some embodiments of the present disclosure.

FIG. 6 is a flowchart illustrating an exemplary process for controlling movement of a table according to some embodiments of the present disclosure. In some embodiments, at least part of process 600 may be performed by the one or more processing devices 140 (implemented in, for example, the computing device 200 shown in FIG. 2). For example, the process 600 may be stored in a storage device (e.g., the storage device(s) 150, the storage 220, the storage 390) in the form of instructions (e.g., an application), and invoked and/or executed by the one or more processing devices 140 (e.g., the processor 210 illustrated in FIG. 2, the CPU 340 illustrated in FIG. 3, or one or more components in the system 500 illustrated in FIG. 5). The operations of the illustrated process presented below are intended to be illustrative. In some embodiments, the process 600 may be accomplished with one or more additional operations not described, and/or without one or more of the operations discussed. Additionally, the order in which the operations of the process 600 as illustrated in FIG. 6 and described below is not intended to be limiting.

The process 600 may illustrate an exemplary process for information communication between the components of the system 500 illustrated in FIG. 5 when the table needs to be moved. In some embodiments, the process 600 may be performed according to a workflow (e.g., a radiation treatment workflow) of the system 500. The workflow may include one or more phases, e.g., one or more image acquisition phases, and/or one or more radiation treatment delivery phases. An image acquisition phase may refer to a phase when the table of a medical apparatus (e.g., the medical apparatus 110) is moved to one or more imaging positions to enable a capture of image data of an object (e.g., a patient) on the table by the first device (e.g., the imaging device 410). At the image acquisition phase, the control of the table may need to be handed over to the first device. A radiation treatment delivery phase may refer to a phase when the table is moved to one or more treatment positions to enable a treatment region of the object to receive radiation delivered by the second device (e.g., the treatment device 412). At the radiation treatment delivery phase, the control of the table may need to be handed over to the second device.

Using the medical apparatus 110, the two phases (i.e., the image acquisition phase and the radiation treatment delivery phase) may be closely connected in time sequences, and the integration of the workflow including the two phases may facilitate the imaging and treatment process of the object. In some embodiments, before a radiation treatment delivery process starts, the workflow may proceed to a first image acquisition phase to detect a position of a target volume (e.g., a tumor) of the object. The table may need to be moved during the first image acquisition phase. The table may be caused to move automatically or by the user. The image acquisition may be initiated automatically or by the user. The image data obtained in the first image acquisition phase may be used to determine a three-dimensional (3D) model of the object including the target volume for radiation treatment. The 3D model of the object and the target volume may be later used to specify a treatment plan. The treatment plan may be configured to guide the treatment of the object in the radiation treatment delivery phase and the positioning of the object with respect to the second device.

In some embodiments, when the radiation treatment delivery process starts, the object may be positioned on the table, and the table may be positioned with respect to the second device according to the treatment plan. Afterwards, the workflow may proceed to a second image acquisition phase to capture image data of the object. In some embodiments, for an MVCT or KVCT, the table may not need to be moved, and the image acquisition may be directly performed. In some embodiments, for a CT on rail, the table may not need to be moved (or the table may need to be moved to an imaging position where the CT on rail can initiate imaging), and the CT device may move along the rail to perform imaging. In some embodiments, for the imaging-treatment apparatuses 400B, 400C, and/or 400D, the table may need to be moved during the second image acquisition phase. The table may be caused to move automatically or by the user. The image acquisition may be initiated automatically or by the user. The image data obtained in the second image acquisition phase may be used to determine a current position of a target volume of the object, and an offset from the position of the target volume relative to the isocenter of the second device may be determined. In some cases (e.g., in an adaptive radiotherapy), whether a shape and/or size of the target volume has changed in comparison with the treatment plan may be determined based on the image data. In some embodiments, a re-planning of the treatment plan may be performed before a radiation treatment delivery phase according to the image data obtained in the second image acquisition phase. In some embodiments, in the re-planning process, the object may be kept on the table. In some embodiments, the second image acquisition phase may be followed by a radiation treatment delivery phase. In some embodiments, in the radiation treatment delivery phase, the table may need to be moved to eliminate the offset, or to satisfy a re-planned treatment plan. In some embodiments, during the radiation treatment delivery process, the radiation treatment delivery may be paused, and the object may be imaged by the first device to monitor the position of the target volume of the object, and thus one or more further image acquisition phases and one or more further radiation treatment delivery phases may alternate.

In some embodiments, the first device and the second device may share a common user interface, or a first user interface associated with the first device and a second user interface associated with the second device may be integrated into a single user interface, so that from the user's point of view, the medical apparatus 110 may function as an integrated apparatus and the workflow of the medical apparatus 110 may be an integrated workflow. In some embodiments, image acquisition may be part of an overall treatment sequence and the user interface may be integrated into a common application or at least the same screen where the workflow is managed.

In 602, one or more first control instructions may be received, by a second control sub-system (e.g., the second control sub-system 520 in FIG. 5), from a first control sub-system (e.g., the first control sub-system 510 in FIG. 5). The first control sub-system 510 and the second control sub-system 520 may control movement of a table (e.g., the table of the medical apparatus 110) shared by the first device and the second device. More descriptions of the configuration of the system of the first device and the second device may be found elsewhere in the present disclosure (e.g., FIG. 5 and descriptions thereof).

The first control sub-system 510 may control the movement of the table when the first device is in its working condition. As described above, in some embodiments, prior to the generation of the treatment plan for the object, the first device may need to scan the object and obtain image data of the object. In some embodiments, prior to or during radiation treatment delivery for the object, the first device may need to scan the object and obtain image data of the object. During an imaging process, the first device may control the movement of the table to scan the object to detect the current position of the target volume (e.g., a tumor) and/or to detect if the shape and/or size of the target volume has changed. If the first device needs to control the table, the first control sub-system 510 may generate the first control instruction(s) and transmit the first control instruction(s) to the second control sub-system 520.

The first control instruction(s) may be configured to control the movement of the table and adjust the position of the table in real time when the first device is controlling the table. In some embodiments, to ensure that the first device collects enough image data of the object, the first control instruction(s) may be used to control the table to perform reciprocating motions. More descriptions of the first control instruction(s) may be found elsewhere in the present disclosure (e.g., FIG. 5 and descriptions thereof).

In some embodiments, the first control instruction(s) may be transmitted from the first control sub-system 510 to the second control sub-system 520 via a point-to-point connection. For example, the first control instruction(s) may be transmitted to the second control sub-system 520 according to a PCIE protocol. In some embodiments, the first control instruction(s) may be included in a first table packet, and the first table packet may be transmitted from the first control sub-system 510 to the second control sub-system 520 (e.g., via a relay station (e.g., the virtual table motion controller 550)). More descriptions of the first table packet may be found elsewhere in the present disclosure (e.g., FIG. 5 and descriptions thereof).

In 604, the first control instruction(s) may be transmitted, by the second control sub-system 520, to a master controller (e.g., the master controller 530) via a point-to-point connection. More descriptions of the point-to-point connection between the first control sub-system 510 and the master controller 530 may be found elsewhere in the present disclosure (e.g., FIG. 5 and descriptions thereof). The transmission of the first control instruction(s) via the point-to-point connection may have a relatively high speed, reducing a transmission latency caused by the relay of the second control sub-system 520. In some embodiments, the latency time between the master controller 530 and the first control sub-system 510 may be less than 10 microseconds. In some embodiments, operations 602 and 604 may be integrated into a single operation. For example, when the first control instruction(s) are transmitted to the second control sub-system 520, the first control instruction(s) may be immediately transmitted to the master controller 530 via the point-to-point connection. It may be unnecessary for the first control instruction(s) to be stored in the second control sub-system 520. In effect, it may seem that the first control instruction(s) are directly transmitted from the first control sub-system 510 to the master controller 530.

In some embodiments, first time information associated with the clock of the first control sub-system 510 may also be transmitted to the master controller 530. In some embodiments, the master controller 530 may assess, based on the first time information, whether the clock of the master controller 530 is synchronized with the clock of the first control sub-system 510. In some embodiments, if the clock of the master controller 530 is not synchronized with the clock of the first control sub-system 510, the master controller 530 may synchronize, based on the first time information, the clock of the master controller 530 with the clock of the first control sub-system 510. In some embodiments, if the clock of the master controller 530 is not synchronized with the clock of the first control sub-system 510, the master controller 530 may report the desynchrony status (or the time information of the master controller 530) to the first control sub-system 510.

In 606, one or more second control instructions may be transmitted, by the second control sub-system 520, to the master controller 530. The second control sub-system 520 may control the movement of the table when the second device is in its working condition. As described above, in some embodiments, before a radiation treatment delivery process, the second control sub-system 520 may need to control the table to move to position the object in a target position according to the treatment plan. In some embodiments, during the radiation treatment delivery process, the second device may control the table to move to place the treatment region of the object under treatment radiation according to the treatment plan. If the second device needs to control the table, the second control sub-system 520 may generate the second control instruction(s) and transmit the second control instruction(s) to the master controller 530. The second control instruction(s) may be configured to control the movement of the table and adjust the position of the table in real time when the second device is controlling the table. In some embodiments, the movement of the table may be determined based on the image data acquired by the first device (i.e., image(s) of the object may guide the movement of the table in a radiation treatment process).

Therefore, the second control instruction(s) may be determined or adjusted based on the image data of the object (or a position of the target volume of the object determined according to the image data). More descriptions of the second control instruction(s) may be found elsewhere in the present disclosure (e.g., FIG. 5 and descriptions thereof). In some embodiments, the second control instruction(s) may be transmitted from the second control sub-system 520 to the master controller 530 via a point-to-point connection. More descriptions of the point-to-point connection may be found elsewhere in the present disclosure (e.g., FIG. 5 and descriptions thereof). In some embodiments, the second control instruction(s) may be included in a second table packet, and the second table packet may be transmitted from the second control sub-system 520 to the master controller 530. More descriptions of the second table packet may be found elsewhere in the present disclosure (e.g., FIG. 5 and descriptions thereof).

In some embodiments, second time information associated with the clock of the second control sub-system 520 may also be transmitted to the master controller 530. In some embodiments, the master controller 530 may assess, based on the second time information, whether the clock of the master controller 530 is synchronized with the clock of the second control sub-system 520. In some embodiments, if the clock of the master controller 530 is not synchronized with the clock of the second control sub-system 520, the master controller 530 may synchronize, based on the second time information, the clock of the master controller 530 with the clock of the second control sub-system 520. In some embodiments, if the clock of the master controller 530 is not synchronized with the clock of the second control sub-system 520, the master controller 530 may report the desynchrony status (or the time information of the master controller 530) to the second control sub-system 520.

In 608, the first control instruction(s) or the second control instruction(s) may be transmitted, by the master controller 530, to a table control sub-system (e.g., the table control sub-system 540). If the master controller 530 receives the first control instruction(s) in operation 604, the received first control instruction(s) may be transmitted to the table control sub-system 540. If the master controller 530 receives the second control instruction(s) in operation 606, the received second control instruction(s) may be transmitted to the table control sub-system 540. It should be noted that the mechanism in FIG. 5 can avoid conflict between the first control sub-system 510 and the second control sub-system 520 in the control of the table (relevant descriptions can be found in FIG. 5), and thus the operations 604 and 606 may not be performed simultaneously or may not be performed in a same phase of the workflow. The master controller 530 may receive either the first control instruction(s) or the second control instruction(s) at one time, and thus the master controller 530 may relay either the first control instruction(s) or the second control instruction(s) to the table control sub-system 540 at one time.

In some embodiments, the master controller 530 may generate third control instruction(s) based on the first control instruction(s) or the second control instruction(s), and transmit the third control instruction(s) to the table control sub-system 540. In some embodiments, either the first control instruction(s) or the second control instruction(s) may be directly designated as the third control instruction(s). More descriptions of the communication between the master controller 530 and the table control sub-system 540 may be found elsewhere in the present disclosure (e.g., FIG. 5 and descriptions thereof).

In some embodiments, the first control sub-system 510 or the second control sub-system 520 may transmit time information to the master controller 530. In some embodiments, the time information may be included in the first table packet or the second table packet. In some embodiments, time information of the master controller 530 may be updated or assessed based on the time information associated with the first control sub-system 510 or the second control sub-system 520. If the first device is controlling the table, the time information of the master controller 530 may be updated according to first time information included in the first table packet associated with the first control instruction(s). If the second device is controlling the table, the time information of the master controller 530 may be updated according to second time information included in the second table packet associated with the second control instruction(s). Therefore, clock synchronization of the first control sub-system 510 (or the second control sub-system 520), and the master controller 530 may be achieved.

In some embodiments, the table control sub-system 540 may assess, based on the first time information (or the second time information), whether the clock of the table control sub-system 540 is synchronized with the clock of the first control sub-system 510 (or the second control sub-system 520). In some embodiments, if the clock of the table control sub-system 540 is not synchronized with the clock of the first control sub-system 510 (or the second control sub-system 520), the table control sub-system 540 may synchronize, based on the first time information (or the second time information), the clock of the table control sub-system 540 with the clock of the first control sub-system 510 (or the second control sub-system 520). In some embodiments, if the clock of the table control sub-system 540 is not synchronized with the clock of the first control sub-system 510 (or the second control sub-system 520), the table control sub-system 540 may report the desynchrony status (or the time information of the table control sub-system 540) to the first control sub-system 510 (or the second control sub-system 520) via the master controller 530. More descriptions of the time information and clock synchronization may be found elsewhere in the present disclosure (e.g., FIG. 5 and descriptions thereof).

In 610, a table (e.g., the table of the medical apparatus 110) may be caused to move, by the table control sub-system 540, according to the first control instruction(s) or the second control instruction(s). In some embodiments, the table control sub-system 540 may generate one or more control signals (e.g., voltage or current signals) based on the first control instruction(s) or the second control instruction(s). The table control sub-system 540 may cause the table to move based on the control signal(s). Therefore, if the first device is controlling the table, the table can be moved according to the first control instruction(s) to perform the first prescribed motion profile. If the second device is controlling the table, the table can be moved according to the second control instruction(s) to perform the second prescribed motion profile.

In 612, movement information of the table may be received, by the master controller 530, from the table control sub-system 540. In some embodiments, motion statuses of the table may be determined in real time, by the table control sub-system 540, when the table is under the control of the first device or the second device. In some embodiments, the motion status of the table may indicate an actual motion profile of the table. As described in FIG. 5, the motion statuses of the table may include a current position of the table, a moving direction of the table, a moving distance of the table, a trajectory of the table, a velocity of the table, an angular velocity of the table, a locked/unlocked status of the table, a motion enable state of the table, a fault flag (if any), or the like, or any combination thereof. As used herein, the position (or velocity, acceleration, etc.) of the table may refer to a position (or velocity, acceleration, etc.) of the table at a time point on a basis of a clock of the table control sub-system 540. In some embodiments, information relating to the motion statuses of the table (also referred to as the movement information of the table) may be transmitted by the table control sub-system 540 in real time or at fixed intervals. In some embodiments, the information relating to the motion statuses may be included in a feedback table packet, and the feedback table packet may be transmitted from the table control sub-system 540 to the master controller 530. The feedback table packet may refer to a data packet returned from the table control sub-system 540. In some embodiments, the master controller 530 may transmit the feedback table packet to the second control sub-system 520.

In some embodiments, the feedback table packet may further include time information (e.g., a timestamp for an event occurred in or relating to the table control sub-system 540) associated with the table control sub-system 540. In some embodiments, the feedback time information may include clock synchronization information indicating the clock of the table control sub-system 540. In some embodiments, upon receiving the time information of the table control sub-system 540, the master controller 530 may assess whether the clock of the table control sub-system 540 is synchronized with the master controller 530. In some embodiments, if it is determined that the clock of the table control sub-system 540 is not synchronized with the master controller 530, the master controller 530 may generate a warning information associated with the desynchrony between the clock of the table control sub-system 540 and the clock of the master controller 530. In some embodiments, the master controller 530 may further transmit the warning information to the second control sub-system 520. In some embodiments, the master controller 530 may package the warning information into the feedback table packet, and transmit the feedback table packet to the second control sub-system 520.

In 614, the movement information of the table may be received, by the second control sub-system 520, from the master controller 530. In some embodiments, the movement information of the table may be transmitted to the second control sub-system 520 immediately (or in real time) based on the communication protocol (e.g., the PCIE protocol) therebetween. In some embodiments, the time information associated with the master controller 530, and/or the table control sub-system 540 may be transmitted from the master controller 530 to the second control sub-system 520. In some embodiments, the movement information of the table and the time information associated with the master controller 530, and/or the table control sub-system 540 may be included in a data packet, and the data packet may be transmitted from the master controller 530 to the second control sub-system 520.

If the second device is controlling the table, the second control sub-system 520 may receive the movement information of the table, and/or the time information associated with the master controller 530 and/or the table control sub-system 540. In some embodiments, the second control sub-system 520 may assess whether an actual motion profile (or a portion thereof (e.g., an actual trajectory)) of the table is in accordance with the prescribed motion profile (or a portion thereof (e.g., the prescribed trajectory)) of the table. The actual motion profile of the table may be determined based on the movement information. If the actual motion profile deviates by more than a specified tolerance from the preset motion profile, the actual motion profile of the table may be determined to deviate from the prescribed motion profile of the table. In response to a determination that the actual motion profile of the table deviates from the prescribed motion profile of the table, the table may be locked by the second control sub-system 520, and thus the table may be in the locked status. In some embodiments, the second control sub-system 520 may assess, based on the received time information, whether the clock of the master controller 530, and/or the clock of the table control sub-system 540 are synchronized with the clock of the second control sub-system 520. If it is determined that the clock of the master controller 530, and/or the clock of the table control sub-system 540 are not synchronized with the clock of the second control sub-system 520, a fault flag may be generated. Further, the second control sub-system 520 may synchronize the clock of the master controller 530 and/or the clock of the table control sub-system 540 with the clock of the second control sub-system 520. Alternatively, the second control sub-system 520 may transmit its own time information to the master controller 530 and/or the table control sub-system 540 to make the master controller 530 and/or the table control sub-system 540 to synchronize their clocks with the second control sub-system 520.

If the first device is controlling the table, the process 600 may proceed to 616. In 616, the movement information of the table, and/or the time information associated with the master controller 530 and/or the table control sub-system 540 may be transmitted, by the second control sub-system 520 or the master controller 530, to the first control sub-system 510, via the point-to-point connection, and the first control sub-system 510 may receive the movement information (and/or the time information). In some embodiments, as described in FIG. 5, the movement information and/or the time information may be transmitted from the master controller 530 to the first control sub-system 510 via the second control sub-system 520 (or a PCIE card thereof). In some embodiments, the second control sub-system 520 may decode the movement information and/or the time information and transmit the information to the virtual table motion controller 550. In some embodiments, the virtual table motion controller 550 may convert the information into a CAN or CANOpen protocol, and relay the converted information to the first control sub-system 510. In some embodiments, if the first device is controlling the table, operations 614 and 616 may be integrated into a single operation. For example, when the data packet is transmitted to the master controller 530, the movement information and/or the time information may be immediately transmitted to the first control sub-system 510 via the point-to-point connection (e.g., the master controller 530, the second control sub-system 520, and the virtual table motion controller 550). It may be unnecessary for the data packet to be stored in the second control sub-system 520. In effect, it may seem that the data packet is directly transmitted from the master controller 530 to the first control sub-system 510. More descriptions of the communication between the master controller 530 and the first control sub-system 510 may be found elsewhere in the present disclosure (e.g., FIG. 5 and descriptions thereof).

In some embodiments, the first control sub-system 510 may assess whether an actual motion profile (or a portion thereof (e.g., an actual trajectory)) of the table is in accordance with the prescribed motion profile (or a portion thereof (e.g., the prescribed trajectory)) of the table. More descriptions regarding the determination of whether the actual motion profile of the table is in accordance with the prescribed motion profile of the table may be found elsewhere in the present disclosure and may not be repeated herein. In response to a determination that the actual motion profile of the table deviates from the prescribed motion profile of the table, the table may be locked by the second control sub-system 520, and thus the table may be in the locked status. In some embodiments, the first control sub-system 510 may assess, based on the received time information, whether the clock of the master controller 530, and/or the clock of the table control sub-system 540 are synchronized with the clock of the first control sub-system 510. If it is determined that the clock of the master controller 530, and/or the clock of the table control sub-system 540 are not synchronized with the clock of the first control sub-system 510, a fault flag may be generated. Further, the first control sub-system 510 may synchronize the clock of the master controller 530 and/or the clock of the table control sub-system 540 with the clock of the first control sub-system 510. Alternatively, the first control sub-system 510 may transmit its own time information to the master controller 530 and/or the table control sub-system 540 to make the master controller 530 and/or the table control sub-system 540 to synchronize their clocks with the first control sub-system 510.

It should be noted that the above description of the process 600 is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, if the second device is in its working condition, operations 602, 604, and 616 may be omitted. As another example, if the first device is in its working condition, operation 606 may be omitted. In some embodiments, before operation 602 or 606, an initialization operation may be performed on the system 500 to synchronize the clock of the first control sub-system 510, the clock of the second control sub-system 520, the clock of the master controller 530, and/or the clock of the table control sub-system 540. In some embodiments, the synchronization may be performed only once when the system 500 is initialized, and time information may not be transmitted between the first control sub-system 510, the second control sub-system 520, the master controller 530, and/or the table control sub-system 540 in the image acquisition phase(s), and/or the radiation treatment delivery phase(s). In some embodiments, time information may be transmitted from the master controller 530, and/or the table control sub-system 540 to the first control sub-system 510 (and/or the second control sub-system 520) only if the clock of the master controller 530, and/or the clock of the table control sub-system 540 are not synchronized with the clock of the first control sub-system 510 (and/or the clock of the second control sub-system 520). In some embodiments, the first control sub-system 510 (or the second control sub-system 520) may generate two or more motion profiles. For example, a first motion profile may specify that the table moves in the Y-axis direction at a first velocity and starts at a first time point, and a second motion profile may specify that the table moves in the Z-axis direction at a second velocity and starts at a second time point. Corresponding to the two or more motion profiles, two or more control instructions may be generated and transmitted to the master controller 530, and/or the table control sub-system 540 in two or more times. Accordingly, one or more operations of process 600 may be performed repeatedly. Merely by way of example, if the second control sub-system 520 is controlling the table, and after the table is moved according to a first motion profile by performing operations 606-614, the second control sub-system 520 may perform operations 606-614 again to transmit a second motion profile to the table control sub-system 540 and cause the table to move to perform the second motion profile.

FIG. 7 is a block diagram illustrating a second exemplary system of the medical apparatus 110 according to some embodiments of the present disclosure. As illustrated in FIG. 7, the system 700 may be part of the one or more processing devices 140. The system 700 may control the movement of a table of the medical apparatus 110. In some embodiments, similar to FIGS. 4A-4D, the table may be shared by a first device (e.g., an imaging device) and a second device (e.g., a treatment device). The system 700 may include a first control sub-system 710 associated with the first device, a second control sub-system 720 associated with the second device, a master controller 730, and a table control sub-system 740.

In some embodiments, the first device may be associated with the first control sub-system 710, the virtual table motion controller 750, the master controller 730, and the table control sub-system 740. The second device may be associated with the second control sub-system 720, the master controller 730, and the table control sub-system 740. In some embodiments, the table control sub-system 740 may be operably coupled to the table. The master controller 730 may be operably connected to the table control sub-system 740. For example, the master controller 730 may be connected to the table control sub-system 740 via an electrical cable, and the communication between the master controller 730 and the table control sub-system 740 may be performed based on a controller area network (CAN) protocol. The first control sub-system 710 may be operably connected to the master controller 730 via the virtual table motion controller 750. For example, the first control sub-system 710 may be connected to the master controller 730 via a peripheral component interconnect express (PCIE) cable, and the communication between the first control sub-system 710 and the master controller 730 may be performed based on a PCIE protocol. In some embodiments, the first control sub-system 710 may communicate (via one or more relay stations (e.g., the virtual table motion controller 750 and/or the master controller 730)) with the table control sub-system 740 through a CAN or CANOpen protocol. In some embodiments, the virtual table motion controller 750 may be configured to tunnel the CAN or CANOpen protocol into a PCIE packet (also referred to a first table packet) to adapt to the point-to-point connection (between the first control sub-system 710 and the master controller 730) on the basis of the PCIE protocol. The virtual table motion controller 750 may function as a relay station. In some embodiments, the virtual table motion controller 750 may send the PCIE packet directly to the master controller 730. In some embodiments, the master controller 730 may convert the PCIE packet back into the CAN or CANOpen protocol, and send the packet to the table control sub-system 740, and then the table control sub-system 740 may control the table based on the instruction(s) from the first control sub-system 710.

In some embodiments, when the first control sub-system 710 is controlling the table, the virtual table motion controller 750 may send the PCIE packet directly to the master controller 730, and the PCIE packet may not be sent to the second control sub-system 720 and/or decoded by the second control sub-system 720.

The second control sub-system 720 may be operably connected to the master controller 730. For example, the second control sub-system 720 may be connected to the master controller 730 via a peripheral component interconnect express (PCIE) cable, and the communication between the second control sub-system 720 and the master controller 730 may be performed based on a PCIE protocol. In some embodiments, the first control sub-system 710 may be part of the terminal 130. In some embodiments, the first control sub-system 710 may be part of the processing device 140. In some embodiments, the second control sub-system 720 may be part of the terminal 130. In some embodiments, the second control sub-system 720 may be part of the processing device 140.

The first control sub-system 710 may be configured to control the first device to perform one or more functionalities (e.g., gantry rotation, imaging of an object) and control the movement of the table to cause one or more desired functionalities to be performed on the object. In some embodiments, when the first control sub-system 710 is controlling or needs to control the table (or the first device is in its working condition), the first control sub-system 710 may generate one or more control commands (also referred to as first control instructions) to control the movement of the table. The second control sub-system 720 may be configured to control the second device to perform one or more functionalities (e.g., beam on/off, radiation dose control, gantry angle adjustment, and/or aperture shape formation of a collimator in radiation treatment of the object) and control the movement of the table to cause one or more desired functionalities to be performed on the object. In some embodiments, when the second control sub-system 720 is controlling or needs to control the table (or the second device is in its working condition), the second control sub-system 720 may generate one or more control commands (also referred to as second control instructions) to control the movement of the table. In some embodiments, the table may be caused to move according to the first control instruction(s). For example, the table may be moved in real time to facilitate an acquisition of image data of the object by the first device. In some embodiments, the table may be caused to move according to the second control instruction(s). For example, the table may be moved in real time to facilitate a radiation treatment of the object by the second device. More descriptions of the first control instruction(s) and the second control instruction(s) may be found elsewhere in the present disclosure (e.g., FIGS. 5-6 and descriptions thereof).

In some embodiments, the master controller 730 may be configured to relay the control commands from the first control sub-system 710 or the second control sub-system 720 to the table control sub-system 740 to control the movement of the table. In some embodiments, the master controller 730 may be further configured to relay information relating to table statuses received from the table control sub-system 740 to the first control sub-system 710 or the second control sub-system 720. The table control sub-system 740 may be configured to directly control the movement of the table. The table control sub-system 740 may be similar to the table control sub-system 540, and relevant descriptions will not be repeated herein.

The first control sub-system 710 may control the movement of the table when the first device is in its working condition. To control the movement of the table, the first control sub-system 710 may generate a first table packet and transmit the first table packet to the master controller 730. The second control sub-system 720 may control the movement of the table when the second device is in its working condition. To control the movement of the table, the second control sub-system 720 may generate a second table packet and transmit the second table packet to the master controller 730. More descriptions of the first table packet and the second table packet may be found elsewhere in the present disclosure (e.g., FIGS. 5-6 and descriptions thereof).

In some embodiments, in the configuration of the system 700, the master controller 730 may be not only a relay station but also a real controller. In some embodiments, the master controller 730 may decide or determine whether the table packet it receives is from the first control sub-system 710 without the advise or intervention of second control sub-system 720. This configuration can make the second control sub-system 720 more independent, i.e., the second control sub-system 720 does not need to deal at all with the operations of the first control sub-system 710. The second control sub-system 720 may not receive information communicated between the first control sub-system 710 and the table control sub-system 740.

In some embodiments, upon receiving the (first or second) table packet, the master controller 730 may parse the (first or second) table packet, and/or transmit a portion or all of the information (e.g., the first or second control instruction(s), the first or second time information) in the (first or second) table packet to the table control sub-system 740. In some embodiments, upon receiving the information transmitted from the master controller 730, the table control sub-system 740 may generate one or more control signals based on the received information (e.g., the first or second control instruction(s)) and cause the table to move based on the control signal(s) so that the table can move according to a first or second prescribed motion profile.

In some embodiments, the table control sub-system 740 may detect motion statuses of the table and transmit information relating to the motion statuses to the master controller 730. More descriptions of the information relating to the motion statuses of the table may be found elsewhere in the present disclosure (e.g., FIGS. 5-6 and descriptions thereof). In some embodiments, the table control sub-system 740 may transmit time information of the table control sub-system 740 or clock synchronization information (e.g., whether the clock of the table control sub-system 740 is synchronized) to the master controller 730. In some embodiments, the master controller 730 may transmit the information received from the table control sub-system 740 to the first control sub-system 710 or the second control sub-system 720 that is controlling the table. In some embodiments, the master controller 730 may transmit clock synchronization information (e.g., whether the clock of the master controller 730 is synchronized) to the first control sub-system 710 or the second control sub-system 720 that is controlling the table. In some embodiments, upon receiving information transmitted from the master controller 730, the first control sub-system 710 or the second control sub-system 720 that is controlling the table may assess whether an actual motion profile (or a portion thereof (e.g., an actual trajectory)) of the table is in accordance with the prescribed motion profile (or a portion thereof (e.g., the prescribed trajectory)) of the table. If the actual motion profile deviates by more than a specified tolerance from the prescribed motion profile, the actual motion profile of the table may be determined to deviate from the prescribed motion profile of the table In response to a determination that the actual motion profile of the table deviates from the prescribed motion profile of the table, the table may be locked by the first control sub-system 710 or the second control sub-system 720 that is controlling the table, and thus the table may be in the locked status. In some embodiments, the first control sub-system 710 or the second control sub-system 720 that is controlling the table may assess, based on the received time information, whether the clock of the master controller 730, and/or the clock of the table control sub-system 740 are synchronized with the clock of the first control sub-system 710 or the second control sub-system 720 that is controlling the table. In response to a determination that the clock of the master controller 730 and/or the clock of the table control sub-system 740 are not synchronized with the clock of the first control sub-system 710 or the second control sub-system 720 that is controlling the table, a fault flag may be generated. Further, the first control sub-system 710 or the second control sub-system 720 that is controlling the table may synchronize the clock of the master controller 730 and/or the clock of the table control sub-system 740 with the clock of the first control sub-system 710 or the second control sub-system 720 that is controlling the table. Alternatively, the first control sub-system 710 or the second control sub-system 720 that is controlling the table may transmit its own time information to the master controller 730 and/or the table control sub-system 740 to make the master controller 730 and/or the table control sub-system 740 to synchronize their clocks with the first control sub-system 710 or the second control sub-system 720 that is controlling the table.

It should be noted that the clock synchronization between the table with the first control sub-system 710 and the second control sub-system 720 may be necessary (even if the first control sub-system 710 and the second control sub-system 720 are not sharing the table). In some embodiments, time synchronization may be not specific to the configurations of the system 500, the system 700, and the system 900. In some embodiments, time synchronization may be common in the imaging device and the treatment device. Therefore, the configurations of the system 500, the system 700, and the system 900 may be universal in that they work for both the imaging device and the treatment device, even if the imaging device and the treatment device are not sharing the table. That is, there is no need to have a special version of control system for the imaging device and the treatment device when they are sharing the table using the configurations illustrated in the present disclosure.

In some embodiments, the second control sub-system 720 may include a smart switch mechanism. Using the smart switch mechanism, the master controller 730 may switch between a first functional connection with the first control sub-system 710 and a second functional connection with the second control sub-system 720. If the smart switch mechanism is switched to the first functional connection with the first control sub-system 710, the communication between the first control sub-system 710, the virtual table motion controller 750, the master controller 730, and the table control sub-system 740 may be activated, while the second control sub-system 720 may be in a stand-by state. Therefore, the first table packet can be transmitted from the first control sub-system 710 to the master controller 730 (via the virtual table motion controller 750) and then the table control sub-system 740, and the feedback table packet can be transmitted from the table control sub-system 740 to the master controller 730 and then the first control sub-system 710 (via the virtual table motion controller 750), while the second control sub-system 720 may be bypassed in the information transmission. Similarly, if the smart switch mechanism is switched to the second functional connection with the second control sub-system 720, the communication between the second control sub-system 720, the master controller 730, and the table control sub-system 740 may be activated, while the first control sub-system 710 may be in a stand-by state. Therefore, the second table packet can be transmitted from the second control sub-system 720 to the master controller 730 and then the table control sub-system 740, and the feedback table packet can be transmitted from the table control sub-system 740 to the master controller 730 and then the second control sub-system 720, while the first control sub-system 710 may be bypassed in the information transmission. In some embodiments, the smart switch mechanism of the second control sub-system 720 may directly transfer the table packet (or feedback table packet) based on a node destination, i.e., a destination of the table packet (or feedback table packet). For example, if the table packet is from the first control sub-system 710, the destination is the table control sub-system 740 via the master controller 730, then according to the smart switch mechanism, the virtual table motion controller 750 may relay the table packet directly to the master controller 730, without the involvement of the second control sub-system 720.

With the smart switch mechanism of the master controller 730, control of the table can be switched between the first control sub-system 710 and the second control sub-system 720, and the table can be controlled by only one of the first control sub-system 710 and second control sub-system 720 at any time, avoiding any conflict between the first control sub-system 710 and the second control sub-system 720. In some embodiments, the smart switch mechanism may work based on the control instruction(s) (either the first control instruction(s) or the second control instruction(s)) received by the master controller 730, a current control status of the table (e.g., whether the table is already controlled by one of the first control sub-system 710 and the second control sub-system 720), a destination of the (feedback) table packet, and/or a workflow of the system 700. In some embodiments, the smart switch mechanism may work based on one or more preset rules. An exemplary preset rule may include priorities of the first control sub-system 710 and the second control sub-system 720 under different situations. For example, during a radiation treatment delivery process, the priority of the imaging device may be set higher than that of the treatment device, that is to say, during the radiation treatment delivery process, whenever the imaging device needs to control the table, the control of the table may be switched to the first control sub-system 710. As another example, when no device is controlling the table, the first control sub-system 710 and the second control sub-system 720 may have an equal priority, that is, the control of the table may be switched to a first one of the first control sub-system 710 and the second control sub-system 720 that transmits control instruction(s) to the master controller 730. In some embodiments, the master controller 730 may determine a priority of the first control sub-system 710 and the second control sub-system 720 based on the control status of the table. In some embodiments, a control sub-system that is controlling the table may have a relatively high priority. For example, if the master controller 730 receives the first control instruction(s) from the first control sub-system 710, and the table is not controlled by the second control sub-system 720 (i.e., the second control sub-system 720 has a relatively low or equal priority), then the smart switch mechanism may switch to the first functional connection with the first control sub-system 710. As another example, if the master controller 730 receives the first control instruction(s) from the first control sub-system 710, and the table is already controlled by the second control sub-system 720 (i.e., the second control sub-system 720 has a relatively high priority, and the smart switch mechanism has already been switched to the second functional connection with the second control sub-system 720), then the master controller 730 may determine that the smart switch mechanism maintains the second functional connection with the second control sub-system 720. In this case, the master controller 730 may inform the first control sub-system 710 to wait until the second control sub-system 720 surrenders control of the table. As still another example, if the master controller 730 receives the second control instruction(s) from the second control sub-system 720, and the table is not controlled by the first control sub-system 710 (i.e., the first control sub-system 710 has a relatively low or equal priority), then the smart switch mechanism may switch to the second functional connection with the second control sub-system 720. As a further example, if the master controller 730 receives the second control instruction(s) from the second control sub-system 720, and the table is already controlled by the first control sub-system 710 (i.e., the first control sub-system 710 has a relatively high priority, and the smart switch mechanism has already been switched to the first functional connection with the first control sub-system 710), then the master controller 730 may determine that the smart switch mechanism maintains the first functional connection with the first control sub-system 710. In this case, the master controller 730 may inform the second control sub-system 720 to wait until the first control sub-system 710 surrenders control of the table.

In some embodiments, the workflow of the system 700 may be similar to the workflow of the system 500. An exemplary workflow is described in FIG. 6, and relevant descriptions may not be repeated herein. In different phases of the workflow, different devices may control the table. For example, in an image acquisition phase, the first device may capture images of the object. In a radiation treatment delivery phase, the second device may treat the object with prescribed treatment beams. If the workflow proceeds to a phase in which the first device needs to control the table, the smart switch mechanism may switch to the first functional connection with the first control sub-system 710. If the workflow proceeds to a phase in which the second device needs to control the table, the smart switch mechanism may switch to the second functional connection with the second control sub-system 720. In some embodiments, the workflow of the system 700 may automatically proceed from a first phase to a second phase. For example, at the end of the first phase (e.g., an imaging phase controlled by the first control sub-system 710), the master controller 730 may inform a corresponding control sub-system (e.g., the second control sub-system 720) to get into its working condition and prepare for the second phase (e.g., a radiation treatment delivery phase), and the smart switch mechanism may be switched to the second functional connection with the second control sub-system 720. In some embodiments, the workflow of the system 700 may be caused to proceed from a first phase to a second phase by a manual operation. For example, when the table is caused by a first user instruction to be moved to an imaging position, the first device may be activated automatically or by a second user instruction, and the smart switch mechanism may be switched to the first functional connection with the first control sub-system 710.

As another example, when the table is caused by a third user instruction to be moved to a treatment position, the second device may be activated automatically or by a fourth user instruction, and the smart switch mechanism may be switched to the second functional connection with the second control sub-system 720.

From the point of view of the first control sub-system 710, the second control sub-system 720 appears dormant or non-existent, the first control sub-system 710 is directly connected to a table motion controller, and the first control sub-system 710 can control the movement of the table by transmitting corresponding control commands to the table motion controller (via one or more relay stations (e.g., the virtual table motion controller 750, the master controller 730)). From the point of view of the second control sub-system 720, the first control sub-system 710 appears dormant or non-existent, the second control sub-system 720 is directly connected to a table motion controller, and the second control sub-system 720 can control the movement of the table by transmitting corresponding control commands to the table motion controller. In FIG. 7, the curved arrows between the master controller 730 and the virtual table motion controller 750 may indicate the smart switch mechanism on the second control sub-system 720. In some embodiments, the smart switch mechanism may be integrated in the master controller 730. In some embodiments, from the point of view of the first control sub-system 710, the virtual table motion controller 750 may function as a relay station that can relay the first table packet directly to the master controller 730 bypassing the second control sub-system 720. Therefore, the first control sub-system 710 and the master controller 730 may communicate, through the virtual table motion controller 750, with a relatively low latency. Because the second control sub-system 720 does not need to process commands or information between the first control sub-system 710 and the table control sub-system 740 when the first control sub-system 710 is in control of the table, the implementation of the second control sub-system 720 may be simplified. In this configuration of the system 700, the first control sub-system 710 may be trusted to behave, and there is no need for the second control sub-system 720 to supervise the first control sub-system 710 as far as the table control is concerned.

With the smart switch mechanism illustrated in FIG. 7, control commands may be filtered based on a function (e.g., an imaging function, a treatment function) that needs to have control of the table motion during a specific phase of the workflow. Taking a CT-RT apparatus as an example, before treatment delivery and when the object is to be imaged, the control may be switched to the CT control sub-system for image acquisition and processing, and once this sequence is finished, the control may be switched to the RT control sub-system. When the RT control sub-system needs to take control of the table, the virtual table motion controller 750 may hide (or shield) this control from the CT control sub-system. When the CT control sub-system needs to retake control, the motion statuses of the table may be reported to the CT control sub-system, and the CT control sub-system can retake control. When the CT control sub-system takes control, the RT control sub-system may surrender control, and the RT control sub-system may be bypassed and communication may be done directly between the virtual table motion controller 750 communicating with the CT controller and the master controller 730 communicating with the table control sub-system 740. The communication between the virtual table motion controller 750 and the master controller 730 may have a relatively low latency.

It should be noted that the above description of the system 700 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

Figure 8:
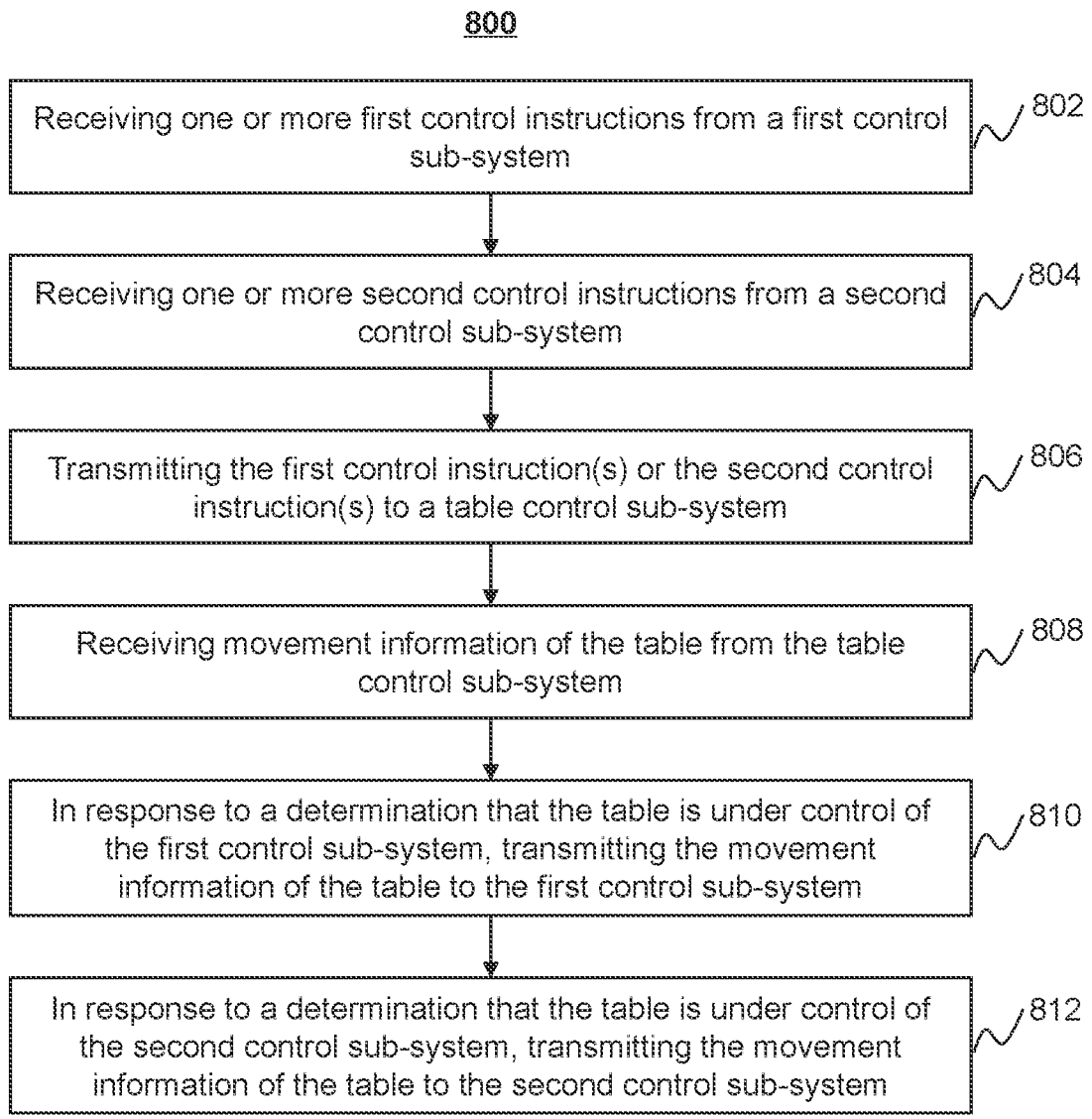
FIG. 8 is a flowchart illustrating an exemplary process for controlling movement of a table according to some embodiments of the present disclosure.

FIG. 8 is a flowchart illustrating an exemplary process for controlling movement of a table according to some embodiments of the present disclosure. In some embodiments, at least part of process 800 may be performed by the one or more processing devices 140 (implemented in, for example, the computing device 200 shown in FIG. 2). For example, the process 800 may be stored in a storage device (e.g., the storage device(s) 150, the storage 220, the storage 390) in the form of instructions (e.g., an application), and invoked and/or executed by the one or more processing devices 140 (e.g., the processor 210 illustrated in FIG. 2, the CPU 340 illustrated in FIG. 3, or one or more components in the system 700 illustrated in FIG. 7). The operations of the illustrated process presented below are intended to be illustrative. In some embodiments, the process 800 may be accomplished with one or more additional operations not described, and/or without one or more of the operations discussed. Additionally, the order in which the operations of the process 800 as illustrated in FIG. 8 and described below is not intended to be limiting.

The process 800 may illustrate an exemplary process for information communication between the components of the system 700 illustrated in FIG. 7 when the table needs to be moved. In some embodiments, one or more operations of the process 800 may be performed before a treatment planning process, and/or during a radiation treatment delivery process.

In 802, one or more first control instructions may be received, e.g., by the master controller 730, from a first control sub-system (e.g., the first control sub-system 710 in FIG. 7). In some embodiments, the first control instructions may be relayed by the virtual table motion controller 750, from the first control sub-system 710 directly to the master controller 730 bypassing the second control sub-system 720. The first control sub-system 710 may control the movement of the table when the first device is in its working condition. In some embodiments, as described in FIG. 6, prior to or during radiation treatment delivery for the object, the first device may need to scan the object and obtain image data of the object. During an imaging process, the first device may control the movement of the table to scan the object to detect the current position of the target volume (e.g., a tumor) and/or to detect if the shape and/or size of the target volume has changed. If the first device needs to control the table, the first control sub-system 710 may generate the first control instruction(s) and transmit the first control instruction(s) to the master controller 730.

The first control instruction(s) may be configured to control the movement of the table and adjust the position of the table in real time when the first device is controlling the table. In some embodiments, to ensure that the first device collects enough image data of the object, the first control instruction(s) may be used to control the table to perform reciprocating motions. More descriptions of the first control instruction(s) may be found elsewhere in the present disclosure (e.g., FIG. 5 and descriptions thereof).

In some embodiments, first time information associated with the clock of the first control sub-system 710 may also be transmitted to the master controller 730. In some embodiments, the master controller 730 may assess, based on the first time information, whether the clock of the master controller 730 is synchronized with the clock of the first control sub-system 710. In some embodiments, if the clock of the master controller 730 is not synchronized with the clock of the first control sub-system 710, the master controller 730 may synchronize, based on the first time information, the clock of the master controller 730 with the clock of the first control sub-system 710. In some embodiments, if the clock of the master controller 730 is not synchronized with the clock of the first control sub-system 710, the master controller 730 may report the desynchrony status (or the time information of the master controller 730) to the first control sub-system 710.

In 804, one or more second control instructions may be received, e.g., by the master controller 730, from a second control sub-system (e.g., the second control sub-system 720). The second control sub-system 720 may control the movement of the table when the second device is in its working condition. As described above, in some embodiments, before a radiation treatment delivery process, the second control sub-system 720 may need to control the table to move to position the object in a target position according to the treatment plan. In some embodiments, during the radiation treatment delivery process, the second device may control the table to move to place the treatment region of the object under treatment radiation according to the treatment plan. If the second device needs to control the table, the second control sub-system 720 may generate the second control instruction(s) and transmit the second control instruction(s) to the master controller 730. The second control instruction(s) may be configured to control the movement of the table and adjust the position of the table in real time when the second device is controlling the table. In some embodiments, the movement of the table may be determined based on the image data acquired by the first device (i.e., image(s) of the object may guide the movement of the table in a radiation treatment process). Therefore, the second control instruction(s) may be determined or adjusted based on the image data of the object (or a position of the target volume of the object determined according to the image data). More descriptions of the second control instruction(s) may be found elsewhere in the present disclosure (e.g., FIG. 5 and descriptions thereof). In some embodiments, the second control instruction(s) may be transmitted from the second control sub-system 720 to the master controller 730 via a point-to-point connection. More descriptions of the point-to-point connection may be found elsewhere in the present disclosure (e.g., FIG. 5 and descriptions thereof). In some embodiments, the second control instruction(s) may be included in a second table packet, and the second table packet may be transmitted from the second control sub-system 720 to the master controller 730. More descriptions of the second table packet may be found elsewhere in the present disclosure (e.g., FIG. 5 and descriptions thereof).

In some embodiments, second time information associated with the clock of the second control sub-system 720 may also be transmitted to the master controller 730. In some embodiments, the master controller 730 may assess, based on the second time information, whether the clock of the master controller 730 is synchronized with the clock of the second control sub-system 720. In some embodiments, if the clock of the master controller 730 is not synchronized with the clock of the second control sub-system 720, the master controller 730 may synchronize, based on the second time information, the clock of the master controller 730 with the clock of the second control sub-system 720. In some embodiments, if the clock of the master controller 730 is not synchronized with the clock of the second control sub-system 720, the master controller 730 may report the desynchrony status (or the time information of the master controller 730) to the second control sub-system 720.

In 806, the first control instruction(s) or the second control instruction(s) may be transmitted, by the master controller 730, to a table control sub-system (e.g., the table control sub-system 740). If the first device is controlling the table, and the master controller 730 receives the first control instruction(s) in operation 802, the received first control instruction(s) may be transmitted to the table control sub-system 740. If the second device is controlling the table, and the master controller 730 receives the second control instruction(s) in operation 804, the received second control instruction(s) may be transmitted to the table control sub-system 740. It should be noted that the mechanism in FIG. 7 can avoid conflict between the first control sub-system 710 and the second control sub-system 720 in the control of the table (relevant descriptions can be found in FIG. 7), and thus the first control instruction(s) and the second control instruction(s) may not be transmitted to the table control sub-system 740 simultaneously or may not be performed in a same phase of the workflow. The master controller 730 may relay either the first control instruction(s) or the second control instruction(s) to the table control sub-system 740 at one time.

In some embodiments, the master controller 730 may generate third control instruction(s) based on the first control instruction(s) or the second control instruction(s), and transmit the third control instruction(s) to the table control sub-system 740. In some embodiments, either the first control instruction(s) or the second control instruction(s) may be directly designated as the third control instruction(s). In some embodiments, the third control instruction(s) may be determined using the smart switch mechanism of the master controller 730. If the control of the table is switched to the first control sub-system 710 by the smart switch mechanism, the first control instruction(s) may be determined as the third control instruction(s). If the control of the table is switched to the second control sub-system 720 by the smart switch mechanism, the second control instruction(s) may be determined as the third control instruction(s). More descriptions of the communication between the master controller 730 and the table control sub-system 740 may be found elsewhere in the present disclosure (e.g., FIG. 7 and descriptions thereof).

In some embodiments, the first control sub-system 710 or the second control sub-system 720 may transmit time information to the master controller 730. In some embodiments, the time information may be included in the first table packet or the second table packet. In some embodiments, time information of the master controller 730 may be updated or assessed based on the time information associated with the first control sub-system 710 or the second control sub-system 720. If the first device is controlling the table, the time information of the master controller 730 may be updated according to first time information included in the first table packet associated with the first control instruction(s). If the second device is controlling the table, the time information of the master controller 730 may be updated according to second time information included in the second table packet associated with the second control instruction(s). In some embodiments, if the clock of the master controller 730 is not synchronized with the clock of the first control sub-system 710 or the second control sub-system 720, the master controller 730 may report the desynchrony status (or the time information of the master controller 730) to the first control sub-system 710 or the second control sub-system 720. Therefore, clock synchronization of the first control sub-system 710 (or the second control sub-system 720), and the master controller 730 may be achieved.

In some embodiments, the table control sub-system 740 may assess, based on the first time information (or the second time information), whether the clock of the table control sub-system 740 is synchronized with the clock of the first control sub-system 710 (or the second control sub-system 720). In some embodiments, if the clock of the table control sub-system 740 is not synchronized with the clock of the first control sub-system 710 (or the second control sub-system 720), the table control sub-system 740 may synchronize, based on the first time information (or the second time information), the clock of the table control sub-system 740 with the clock of the first control sub-system 710 (or the second control sub-system 720). In some embodiments, if the clock of the table control sub-system 740 is not synchronized with the clock of the first control sub-system 710 (or the second control sub-system 720), the table control sub-system 740 may report the desynchrony status (or the time information of the table control sub-system 740) to the first control sub-system 710 (or the second control sub-system 720) via the master controller 730. More descriptions of the time information and clock synchronization may be found elsewhere in the present disclosure (e.g., FIG. 7 and descriptions thereof).

In 808, movement information of the table may be received, by the master controller 730, from the table control sub-system 740. Operation 808 may be similar to operation 612, and relevant descriptions of the movement information and the transmission of the movement information between the table control sub-system 740 and the master controller 730 may be found in FIG. 6 and descriptions thereof.

In 810, in response to a determination that the table is under control of the first control sub-system 710, the movement information of the table may be transmitted, by the master controller 730, to the first control sub-system 710 (via the virtual table motion controller 750) bypassing the second control sub-system 720. For example, if the control of the table is switched to the first control sub-system 710, the movement information may be transmitted to the first control sub-system 710 in real time, by the master controller 730. In some embodiments, if the control of the table is switched from the second control sub-system 720 to the first control sub-system 710 (e.g., the first device retakes the control), at least a portion of the movement information may be transmitted to the first control sub-system 710. For example, the position of the table may be transmitted to the first control sub-system 710. In some embodiments, the time information associated with the master controller 730, and/or the table control sub-system 740 may be transmitted from the master controller 730 to the first control sub-system 710. In some embodiments, the movement information of the table and the time information associated with the master controller 730, and/or the table control sub-system 740 may be included in a data packet, and the data packet may be transmitted from the master controller 730 to the first control sub-system 710.

If the first device is controlling the table, the first control sub-system 710 may receive the movement information of the table, and/or the time information associated with the master controller 730 and/or the table control sub-system 740. In some embodiments, the first control sub-system 710 may assess whether an actual motion profile (or a portion thereof (e.g., an actual trajectory)) of the table is in accordance with the prescribed motion profile (or a portion thereof (e.g., the prescribed trajectory)) of the table. If the actual motion profile deviates by more than a specified tolerance from the prescribed motion profile, the actual motion profile of the table may be determined to deviate from the prescribed motion profile of the table. In response to a determination that the actual motion profile of the table deviates from the prescribed motion profile of the table, the table may be locked by the first control sub-system 710, and thus the table may be in the locked status. In some embodiments, the first control sub-system 710 may assess, based on the received time information, whether the clock of the master controller 730, and/or the clock of the table control sub-system 740 are synchronized with the clock of the first control sub-system 710. If it is determined that the clock of the master controller 730, and/or the clock of the table control sub-system 740 are not synchronized with the clock of the first control sub-system 710, a fault flag may be generated. Further, the first control sub-system 710 may synchronize the clock of the master controller 730, and/or the clock of the table control sub-system 740 with the clock of the first control sub-system 710. Alternatively, the first control sub-system 710 may transmit its own time information to the master controller 730 and/or the table control sub-system 740 to make the master controller 730 and/or the table control sub-system 740 to synchronize their clocks with the first control sub-system 710.

In 812, in response to a determination that the table is under control of the second control sub-system 720, the movement information of the table may be transmitted, by the master controller 730, to the second control sub-system 720. For example, if the control of the table is switched to the second control sub-system 720, the movement information may be transmitted to the second control sub-system 720 in real time, by the master controller 730. In some embodiments, the time information associated with the master controller 730, and/or the table control sub-system 740 may be transmitted from the master controller 730 to the second control sub-system 720. In some embodiments, the movement information of the table and the time information associated with the master controller 730, and/or the table control sub-system 740 may be included in a data packet, and the data packet may be transmitted from the master controller 730 to the second control sub-system 720.

If the second device is controlling the table, the second control sub-system 720 may receive the movement information of the table, and/or the time information associated with the master controller 730, and/or the table control sub-system 740. In some embodiments, the second control sub-system 720 may assess whether an actual motion profile (or a portion thereof (e.g., an actual trajectory)) of the table is in accordance with the prescribed motion profile (e.g., the prescribed trajectory) of the table. In response to a determination that the actual motion profile of the table deviates from the prescribed motion profile of the table, the table may be locked by the second control sub-system 720, and thus the table may be in the locked status. In some embodiments, the second control sub-system 720 may assess, based on the received time information, whether the clock of the master controller 730, and/or the clock of the table control sub-system 740 are synchronized with the clock of the second control sub-system 720. If it is determined that the clock of the master controller 730, and/or the clock of the table control sub-system 740 are not synchronized with the clock of the second control sub-system 720, a fault flag may be generated. Further, the second control sub-system 720 may synchronize the clock of the master controller 730, and/or the clock of the table control sub-system 740 with the clock of the second control sub-system 720. Alternatively, the second control sub-system 720 may transmit its own time information to the master controller 730 and/or the table control sub-system 740 to make the master controller 730 and/or the table control sub-system 740 to synchronize their clocks with the second control sub-system 720.

It should be noted that the above description of the process 800 is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, if the second device is in its working condition, operations 802 and 810 may be omitted. As another example, if the first device is in its working condition, operations 804 and 812 may be omitted. In some embodiments, before operation 802 or 804, an initialization operation may be performed on the system 700 to synchronize the clock of the first control sub-system 710, the clock of the second control sub-system 720, the clock of the master controller 730, and/or the clock of the table control sub-system 740. In some embodiments, the synchronization may be performed only once when the system 700 is initialized, and time information may not be transmitted between the first control sub-system 710 (or the second control sub-system 720), the master controller 730, and/or the table control sub-system 740 in the image acquisition phase(s), and/or the radiation treatment delivery phase(s). In some embodiments, time information may be transmitted from the master controller 730, and/or the table control sub-system 740 to the first control sub-system 710 (or the second control sub-system 720) only if the clock of the master controller 730, and/or the clock of the table control sub-system 740 are not synchronized with the clock of the first control sub-system 710 (or the clock of the second control sub-system 720).

Figure 9:
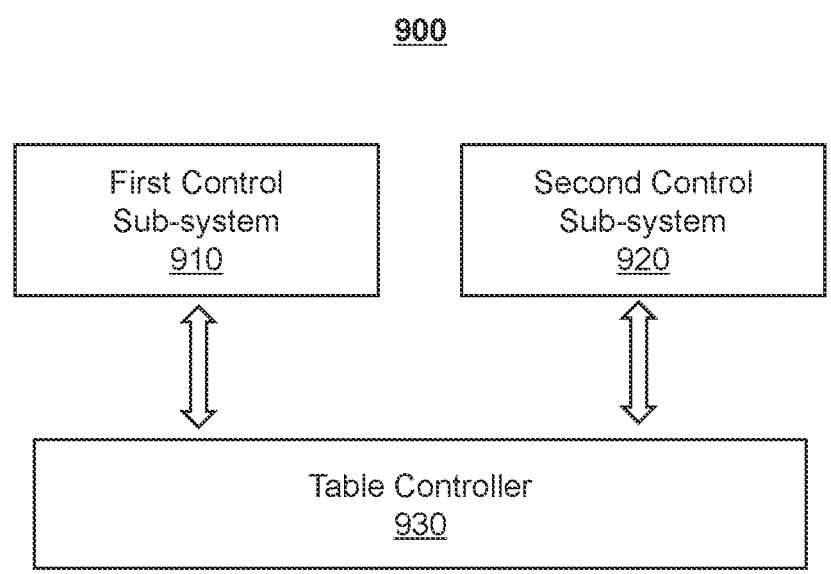

FIG. 9 is a block diagram illustrating a third exemplary system of the medical apparatus 110 according to some embodiments of the present disclosure. The system 900 may be part of the one or more processing devices 140. The system 900 may control the movement of a table of the medical apparatus 110. In some embodiments, similar to FIGS. 4A-4D, the table may be shared by a first device (e.g., an imaging device) and a second device (e.g., a treatment device). The system 900 may include a first control sub-system 910, a second control sub-system 920, and a table controller 930.

The first control sub-system 910 and the second control sub-system 920 may be configured to control movement of the table shared by the first device and the second device. The first control sub-system 910 may be operably coupled to the first device (e.g., an imaging device of the medical apparatus 110). The first control sub-system 910 may control the movement of the table when the first device is in its working condition. The second control sub-system 920 may be operably coupled to the second device (e.g., a treatment device of the medical apparatus 110). The second control sub-system 920 may control the movement of the table when the second device is in its working condition.

The first control sub-system 910 may be configured to control the first device to perform one or more functionalities (e.g., gantry rotation, imaging of an object) and control the movement of the table to cause one or more desired functionalities to be performed on the object. In some embodiments, when the first control sub-system 910 is controlling or needs to control the table (or the first device is in its working condition), the first control sub-system 910 may generate one or more control commands (also referred to as first control instructions) to control the movement of the table. The second control sub-system 920 may be configured to control the second device to perform one or more functionalities (e.g., beam on/off, radiation dose control, gantry angle adjustment, and/or aperture shape formation of a collimator in radiation treatment of the object) and control the movement of the table to cause one or more desired functionalities to be performed on the object. In some embodiments, when the second control sub-system 920 is controlling or needs to control the table (or the second device is in its working condition), the second control sub-system 920 may generate one or more control commands (also referred to as second control instructions) to control the movement of the table. In some embodiments, the table may be caused to move according to the first control instruction(s). For example, the table may be moved in real time to facilitate an acquisition of image data of the object by the first device. In some embodiments, the table may be caused to move according to the second control instruction(s). For example, the table may be moved in real time to facilitate a radiation treatment of the object by the second device. More descriptions of the first control instruction(s) and the second control instruction(s) may be found elsewhere in the present disclosure (e.g., FIGS. 5-8 and descriptions thereof).

The table controller 930 may be operably coupled to the table. The table controller 930 may control the movement of the table and adjust the position of the table in real time. The table controller 930 may control the table to move to a plurality of positions in one or more directions (e.g., the X-axis direction, the Y-axis direction, and/or the Z-axis direction illustrated in FIGS. 1 and 4A-4D). More descriptions of the movement of the table may be found elsewhere in the present disclosure (e.g., FIG. 5 and descriptions thereof). In some embodiments, the table controller 930 may include one or more sub-controllers. More descriptions of the sub-controllers may be found elsewhere in the present disclosure (e.g., FIG. 5 and descriptions thereof). For example, the table controller 930 may include a first sub-controller controlling the axial movements of the table and a second sub-controller controlling the rotational movements of the table. As another example, the table controller 930 may include three sub-controllers, each of which controlling a movement in a certain direction (e.g., the X-axis direction, the Y-axis direction, and/or the Z-axis direction). In some embodiments, the table controller 930 may include a single integrated controller configured to control the different movements (e.g., the axial movements and the rotational movements). In some embodiments, the table controller 930 may further include a driving circuit configured to generate, based on the control signals generated by the table controller 930, a driving force to drive the table to move.

In some embodiments, the table controller 930 may be part of the one or more processing devices 140. In some embodiments, the table controller 930 may be a server (e.g., a single server or a server group). In some embodiments, the table controller 930 may include one or more interfaces. An interface of the table controller 930 may provide a connection interface for a client of the table controller 930. In some embodiments, a device of the medical apparatus 110 may function as a client. For example, the table controller 930 may include a first interface between the table controller 930 and the first device, and/or a second interface between the table controller 930 and the second device. In some embodiments, an interface of the table controller 930 may have a corresponding communication protocol so that the table controller 930 and a client may communicate with each other through the communication protocol. The first interface and the second interface may have the same or different communication protocols.

In some embodiments, the first control sub-system 910 may be operably coupled to the table controller 930 and function as a first client of the table controller 930. For example, the first control sub-system 910 may be operably coupled to the table controller 930 via the first interface of the table controller 930. In some embodiments, if the first device needs to control the table, the first control sub-system 910 may generate control commands and transmit the control commands to the table controller 930 to control the movement of the table. In some embodiments, the second control sub-system 920 may be operably coupled to the table controller 930 and function as a second client of the table controller 930. For example, the second control sub-system 920 may be operably coupled to the table controller 930 via the second interface of the table controller 930. In some embodiments, if the second device needs to control the table, the second control sub-system 920 may generate control commands and transmit the control commands to the table controller 930 to control the movement of the table.

In some embodiments, the table controller 930 may be coupled to only one of the first control sub-system 910 and second control sub-system 920 at any time, or the table controller 930 may respond to the control commands of only one of the first control sub-system 910 and the second control sub-system 920 at any time. In some embodiments, the table controller 930 may include an arbitration mechanism. Using the arbitration mechanism, the table controller 930 may determine to couple to or respond to which one of the first control sub-system 910 and the second control sub-system 920. In some embodiments, the arbitration mechanism may be performed based on one or more preset rules. An exemplary preset rule may include priorities of the first control sub-system 910 and the second control sub-system 920 under different situations. For example, during a radiation treatment delivery process, the priority of the imaging device may be set higher than that of the treatment device, that is to say, during the radiation treatment delivery process, whenever the imaging device needs to control the table, the control of the table may be granted to the first control sub-system 910. As another example, when no device is controlling the table, the first control sub-system 910 and the second control sub-system 920 may have an equal priority, that is, the control of the table may be granted to a first one of the first control sub-system 910 and the second control sub-system 920 that transmits control command(s) to the table controller 930. In some embodiments, the table controller 930 may determine a priority of the first control sub-system 910 and the second control sub-system 920 based on the control status of the table. In some embodiments, a control sub-system that is controlling the table may have a relatively high priority. The priorities of the first control sub-system 910 and the second control sub-system 920 may be similar to the priorities of the first control sub-system 710 and the second control sub-system 720, and relevant descriptions may be found elsewhere in the present disclosure (e.g., FIG. 7 and descriptions thereof). In some embodiments, the arbitration mechanism may work based on a trigger signal transmitted from the first control sub-system 910 or the second control sub-system 920, a current control status of the table (e.g., whether the table is already controlled by one of the first control sub-system 910 and the second control sub-system 920), and/or a workflow of the system 900. With the arbitration mechanism of the table controller 930, control of the table can be switched between the first control sub-system 910 and the second control sub-system 920, and the table can be controlled by only one of the first control sub-system 910 and second control sub-system 920 at any time, avoiding any conflict between the first control sub-system 910 and the second control sub-system 920.

The first control sub-system 910 may control the movement of the table when the first device is in its working condition. To control the movement of the table, the first control sub-system 910 may generate a first table packet and transmit the first table packet to the table controller 930. The second control sub-system 920 may control the movement of the table when the second device is in its working condition. To control the movement of the table, the second control sub-system 920 may generate a second table packet and transmit the second table packet to the table controller 930. More descriptions of the first table packet and the second table packet may be found elsewhere in the present disclosure (e.g., FIGS. 5-8 and descriptions thereof).

In some embodiments, the table controller 930 may communicate with the first control sub-system 910 according to a CAN or CANOpen protocol, and may communicate with the second control sub-system 920 according to a PCIE protocol. In some embodiments, the content of the first table packet transmitted between the first control sub-system 910 and the table controller 930 may be the same as or similar to the content of the first table packet transmitted between the first control sub-system 510 and the table controller sub-system 540, or between the first control sub-system 710 and the table control sub-system 740. In some embodiments, the content of the second table packet transmitted between the second control sub-system 920 and the table controller 930 may be the same as or similar to the content of the second table packet transmitted between the second control sub-system 520 and the table control sub-system 540, or between the second control sub-system 720 and the table control sub-system 740. It should be noted that in order to make it as transparent as possible for the imaging system and the treatment system in the control of the shared device, i.e., the table, the original "packets" generated by the first control sub-system 510, the first control sub-system 710, and the first control sub-system 910 may be the same, and the original "packets" generated by the second control sub-system 520, the second control sub-system 720, and the second control sub-system 920 may be the same. A transport mechanism for the communication packets of the originators (i.e., the imaging system and the treatment system) is provided, and the communication packets of a same originator in different configurations of the present disclosure may be the same regardless of how they are transferred, whether the table is shared or not. In some embodiments, the configurations of the first control sub-system 510, the first control sub-system 710, and the first control sub-system 910 may be the same or similar. In some embodiments, the configurations of the second control sub-system 520, the second control sub-system 720, and the second control sub-system 920 may be the same or similar.

In some embodiments, when the first device needs to take control of the table or is controlling the table, the first control sub-system 910 may further generate a first trigger signal and transmit the first trigger signal to the table controller

930. The first trigger signal may be configured to request the control of the table to the table controller 930 and/or request to synchronize the clock of the first device with the clock of the table controller 930. In some embodiments, when the second device needs to take control of the table or is controlling the table, the second control sub-system 920 may further generate a second trigger signal and transmit the second trigger signal to the table controller 930. The second trigger signal may be configured to request the control of the table to the table controller 930 and/or request to synchronize the clock of the second device with the clock of the table controller 930.

In some embodiments, upon receiving the (first or second) table packet, the table controller 930 may parse the (first or second) table packet, and/or determine information relating to the control of the table (e.g., the first or second control instruction(s), the first or second time information) in the (first or second) table packet. In some embodiments, upon receiving the information transmitted from the first control sub-system 910 or the second control sub-system 920, the table controller 930 may generate one or more control signals based on the received information (e.g., the first or second control instruction(s)) and cause the table to move based on the control signal(s) so that the table can move according to the first or second prescribed motion profile. In some embodiments, if the table controller 930 receive the first control instruction(s) and the second control instruction(s) simultaneously, the control signal(s) may be generated based on the first control instruction(s) or the second control instruction(s) based on the arbitration mechanism mentioned above. In response to a determination that the first device needs to control or is controlling the table, the table controller 930 may generate the control signal(s) based on the first control instruction(s). In response to a determination that the second device needs to control or is controlling the table, the table controller 930 may generate the control signal(s) based on the second control instruction(s).

In some embodiments, the table controller 930 may detect motion statuses of the table and transmit information relating to the motion statuses to the first control sub-system 910 or the second control sub-system 920. In some embodiments, upon receiving movement information (also referred to as information relating to the motion statuses) transmitted from the table controller 930, the first control sub-system 910 or the second control sub-system 920 that is controlling the table may assess whether an actual motion profile (or a portion thereof (e.g., an actual trajectory)) of the table is in accordance with the prescribed motion profile (or a portion thereof (e.g., the prescribed trajectory)) of the table. If the actual motion profile deviates by more than a specified tolerance from the prescribed motion profile, the actual motion profile of the table may be determined to deviate from the prescribed motion profile of the table. In response to a determination that the actual motion profile of the table deviates from the prescribed motion profile of the table, the table may be locked by the first control sub-system 910 or the second control sub-system 920 that is controlling the table, and the table may be in the locked status. More descriptions of the information relating to the motion statuses of the table may be found elsewhere in the present disclosure (e.g., FIGS. 5-8 and descriptions thereof).

In some situations, if the imaging device is controlling the table, the treatment device may perceive that the table is out of control and perceive that is in an illegal state. If the treatment device detects that the table is moving without the control of the treatment device, the table may be interlocked. In some embodiments, in order to make the first control sub-system 910 and the second control sub-system 920 work independently, the table motion may be hidden for the second control sub-system 920 when the first control sub-system 910 is controlling the table. In some embodiments, a control sub-system that is not controlling the table or does not need to control the table, may be in a stand-by state, and may be hidden from the communication between the table controller 930 and the other control sub-systems (or bypassed in the information transmission). For example, the control sub-system that is not controlling the table or does not need to control the table may not receive a position of the table. In alternative embodiments, a control sub-system that is not controlling the table or does not need to control the table, may be in a stand-by state, and may ignore the table motion. For example, when the second control sub-system 920 is in stand-by while the first control sub-system 910 is controlling the table, the second control sub-system 920 may ignore the table motion. However, in some embodiments, the table controller 930 may report a current control status of the table (e.g., whether the table is controlled by any other control sub-system) to the control sub-system that is not controlling the table or does not need to control the table.

In some embodiments, the table controller 930 may assess, based on time information received from the first control sub-system 910 or the second control sub-system 920, whether the clock of the first control sub-system 910 or the second control sub-system 920 is synchronized with the clock of the table controller 930. In some embodiments, the table controller 930 may transmit time information of the table controller 930 or clock synchronization information (e.g., whether the clock of the first control sub-system 910 or the second control sub-system 920 is synchronized with the table controller 930) to the first control sub-system 910 or second control sub-system 920 that is controlling the table. In some embodiments, upon receiving the time information transmitted from the table controller 930, the first control sub-system 910 or the second control sub-system 920 that is controlling the table may synchronize its own clock with the clock of the table controller 930. Alternatively, if the clock of the table controller 930 is not synchronized with the first control sub-system 910 or the second control sub-system 920 that is controlling the table, the table controller 930 may synchronize, based on the time information received from the first control sub-system 910 or the second control sub-system 920 that is controlling the table, its own clock with the clock of the first control sub-system 910 or the second control sub-system 920 that is controlling the table. In some embodiments, the first control sub-system 910 or second control sub-system 920 may assess, based on the time information transmitted from the table controller 930, whether the clock of the first control sub-system 910 or the second control sub-system 920 is synchronized with the clock of the table controller 930. No matter which of the table controller 930 and the first control sub-system 910 (or the second control sub-system 920) verifies the clock synchronization status, in some embodiments, the table controller 930 may synchronize its own clock with the clock of the first control sub-system 910 or the second control sub-system 920 that is controlling the table; in some embodiments, the first control sub-system 910 or the second control sub-system 920 that is controlling the table may synchronize its own clock with the clock of the table controller 930.

With the server-client configuration illustrated in FIG. 9, control of the table may be shared between the first device and the second device. Taking a CT-RT apparatus as an example, the table controller 930 can directly interface with both an RT control sub-system and a CT control sub-system. The table controller 930 may behave as a table server, which can support the RT client (i.e., the RT control sub-system) and the CT client (i.e., the CT control sub-system) based on a current phase in the image and therapy sequence of a treatment delivery workflow. In some embodiments, the table controller 930 may be responsible for synchronizing the clock with the CT control sub-system or the RT control sub-system, and the synchronization can be done based on a trigger signal directly transmitted from the CT control sub-system or the RT control sub-system according to which needs to take control of the table. With the server-client configuration, fast independent communication transports can be realized between the table controller 930 and the CT control sub-system, and between the table controller 930 and the RT control sub-system. With the fast communication therebetween, the synchronization of table motion can be done with a microsecond latency. With the server-client configuration, the RT control sub-system and the CT control sub-system are both clients and do not need to do any synchronization with each other. The table controller 930 can be informed of which sub-system needs to take control of the table, based on a predefined set of rules. The table controller 930 can switch the control of table to either the CT control sub-system or the RT control sub-system. The table controller 930 can also continue to provide feedback to a client that is not in control of the table and can hide the actual position of the table to the client that has relinquished control.

Figure 10:
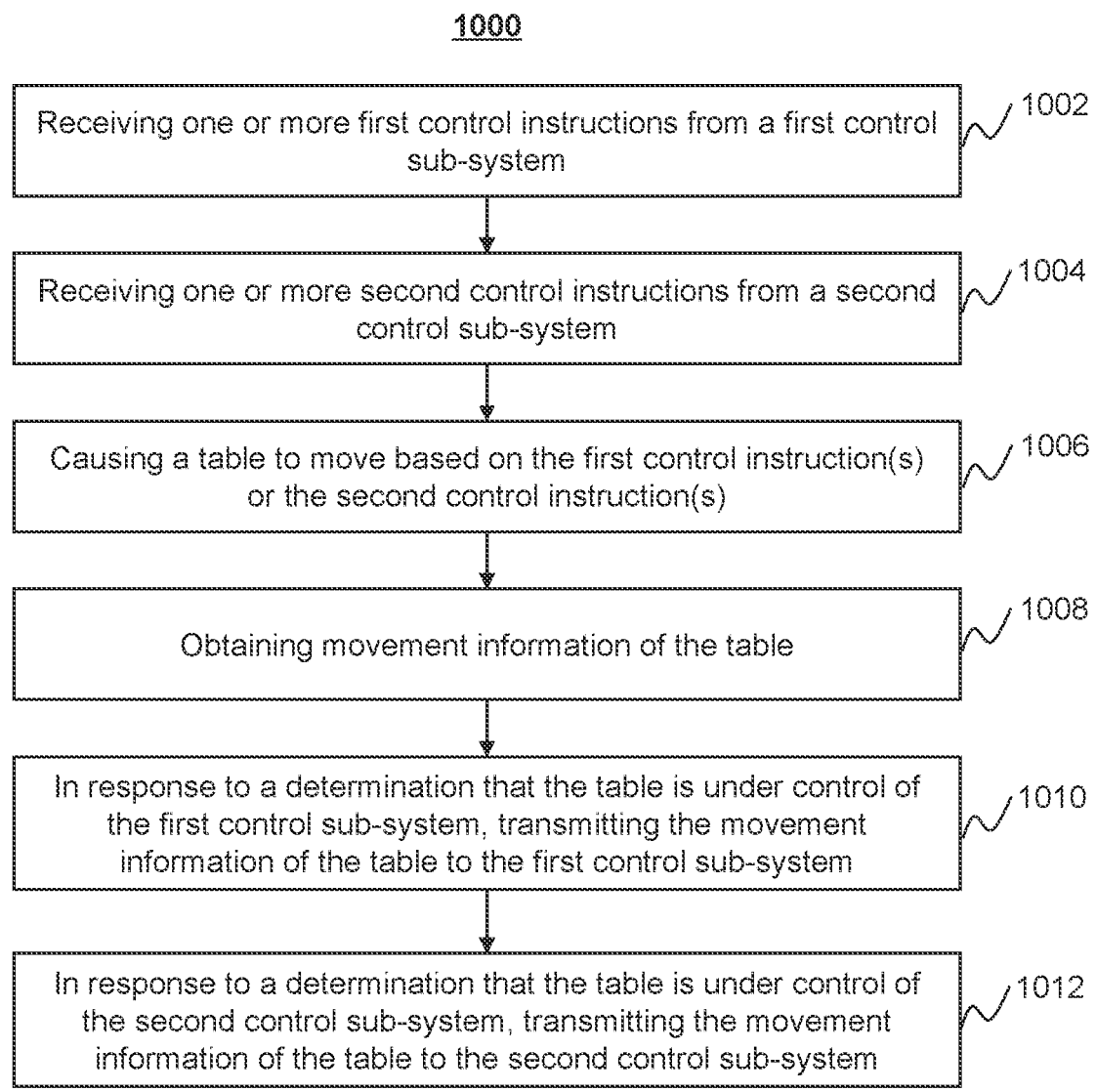
FIG. 10 is a flowchart illustrating an exemplary process for controlling movement of a table according to some embodiments of the present disclosure.

FIG. 10 is a flowchart illustrating an exemplary process for controlling movement of a table according to some embodiments of the present disclosure. In some embodiments, at least part of process 1000 may be performed by the one or more processing devices 140 (implemented in, for example, the computing device 200 shown in FIG. 2). For example, the process 1000 may be stored in a storage device (e.g., the storage device(s) 150, the storage 220, the storage 390) in the form of instructions (e.g., an application), and invoked and/or executed by the one or more processing devices 140 (e.g., the processor 210 illustrated in FIG. 2, the CPU 340 illustrated in FIG. 3, or one or more components in the system 900 illustrated in FIG. 9). The operations of the illustrated process presented below are intended to be illustrative. In some embodiments, the process 1000 may be accomplished with one or more additional operations not described, and/or without one or more of the operations discussed. Additionally, the order in which the operations of the process 1000 as illustrated in FIG. 10 and described below is not intended to be limiting.

The process 1000 may illustrate an exemplary process for information communication between the components of the system 900 illustrated in FIG. 9 when the table needs to be moved. In some embodiments, one or more operations of the process 1000 may be performed before a treatment planning process, and/or during a radiation treatment delivery process.

In some embodiments, the workflow of the system 900 may be similar to the workflow of the system 500. An exemplary workflow is described in FIG. 6, and relevant descriptions may not be repeated herein. In different phases of the workflow, different devices may control the table. For example, in an image acquisition phase, the first device may capture images of the object. In a radiation treatment delivery phase, the second device may treat the object with prescribed treatment beams. More descriptions of the workflow may be found elsewhere in the present disclosure (e.g., FIGS. 5-7 and descriptions thereof).

In 1002, one or more first control instructions may be received, by the table controller 930, from a first control sub-system (e.g., the first control sub-system 910). In some embodiments, the first control sub-system 910 may be operably coupled to the table controller 930 via a first interface of the table controller 930. The first control instruction(s) may be transmitted from the first control sub-system 910 to the table controller 930 via the first interface. Via the first interface, the first control sub-system 910 may act as a client of the table controller 930, while the table controller 930 may act as a server. In some embodiments, as described in FIG. 6, prior to or during radiation treatment delivery for the object, the first device may need to scan the object and obtain image data of the object . . . . During an imaging process, the first device may control the movement of the table to scan the object to detect the current position of the target volume (e.g., a tumor) and/or to detect if the shape and/or size of the target volume has changed. The first control instruction(s) may be generated by the first control sub-system 910 when the first device needs to control the table. The first control instruction(s) may be used to control the movement of the table and adjust the position of the table in real time when the first device is in its working condition. More descriptions of the first control instruction(s) may be found elsewhere in the present disclosure (e.g., FIG. 5 and descriptions thereof).

In some embodiments, first time information associated with the clock of the first control sub-system 910 may also be transmitted to the table controller 930. In some embodiments, the table controller 930 may assess, based on the first time information, whether the clock of the table controller 930 is synchronized with the clock of the first control sub-system 910. In some embodiments, if the clock of the table controller 930 is not synchronized with the clock of the first control sub-system 910, the table controller 930 may synchronize, based on the first time information, the clock of the table controller 930 with the clock of the first control sub-system 910. In some embodiments, if the clock of the table controller 930 is not synchronized with the clock of the first control sub-system 910, the table controller 930 may report the desynchrony status (or the time information of the table controller 930) to the first control sub-system 910.

In 1004, one or more second control instructions may be received, e.g., by the table controller 930, from a second control sub-system (e.g., the second control sub-system 920). In some embodiments, the second control sub-system 920 may be operably coupled to the table controller 930 via a second interface of the table controller 930. The second control instruction(s) may be transmitted from the second control sub-system 920 to the table controller 930 via the second interface. Via the second interface, the second control sub-system 920 may act as a client of the table controller 930, while the table controller 930 may act as a server. The second control sub-system 920 may control the movement of the table when the second device is in its working condition. As described above, in some embodiments, before a radiation treatment delivery process, the second control sub-system 920 may need to control the table to move to position the object in a target position according to the treatment plan. In some embodiments, during the radiation treatment delivery process, the second device may control the table to move to place the treatment region of the object under treatment radiation according to the treatment plan. If the second device needs to control the table, the second control sub-system 920 may generate the second control instruction(s) and transmit the second control instruction(s) to the table controller 930. The second control instruction(s) may be configured to control the movement of the table and adjust the position of the table in real time when the second device is controlling or needs to control the table. In some embodiments, the movement of the table may be determined based on the image data acquired by the first device (i.e., image(s) of the object may guide the movement of the table in a radiation treatment process). Therefore, the second control instruction(s) may be determined or adjusted based on the image data of the object (or a position of the target volume of the object determined according to the image data). More descriptions of the second control instruction(s) may be found elsewhere in the present disclosure (e.g., FIG. 5 and descriptions thereof).

In some embodiments, second time information associated with the clock of the second control sub-system 920 may also be transmitted to the table controller 930. In some embodiments, the table controller 930 may assess, based on the second time information, whether the clock of the table controller 930 is synchronized with the clock of the second control sub-system 920. In some embodiments, if the clock of the table controller 930 is not synchronized with the clock of the second control sub-system 920, the table controller 930 may synchronize, based on the second time information, the clock of the table controller 930 with the clock of the second control sub-system 920. In some embodiments, if the clock of the table controller 930 is not synchronized with the clock of the second control sub-system 920, the table controller 930 may report the desynchrony status (or the time information of the table controller 930) to the second control sub-system 920.

In 1006, a table (e.g., the table of the medical apparatus 110) may be caused, by the table controller 930, to move based on the first control instruction(s) or the second control instruction(s). In some embodiments, one or more control signals may be generated, by the table controller 930, based on the first control instruction(s) or the second control instruction(s). The table may be caused to move based on the control signal(s). More descriptions of the control signal(s) and the generation of the control signal(s) may be found elsewhere in the present disclosure (e.g., FIG. 9 and descriptions thereof).

In 1008, movement information of the table may be obtained by the table controller 930. More descriptions of the movement information of the table and the obtaining of the movement information may be found elsewhere in the present disclosure (e.g., FIGS. 5-9 and descriptions thereof).

In 1010, in response to a determination that the table is under control of the first control sub-system 910, the movement information of the table may be transmitted, by the table controller 930, to the first control sub-system 910. In some embodiments, a portion of the information relating to the motion status of the table may be transmitted to the second control sub-system 920. For example, the current position of the table may not be transmitted to the second control sub-system 920 while the control status of the table (e.g., the table is controlled by the first control sub-system 910) may be transmitted to the second control sub-system 920. In some embodiments, the time information associated with the table controller 930 may be transmitted from the table controller 930 to the first control sub-system 910. In some embodiments, the movement information of the table and the time information associated with the table controller 930 may be included in a data packet, and the data packet may be transmitted from the table controller 930 to the first control sub-system 910.

If the first device is controlling the table, the first control sub-system 910 may receive the movement information of the table, and/or the time information associated with the table controller 930. In some embodiments, the first control sub-system 910 may assess whether an actual motion profile (or a portion thereof (e.g., an actual trajectory)) of the table is in accordance with the prescribed motion profile (or a portion thereof (e.g., the actual trajectory)) of the table. If the actual motion profile deviates by more than a specified tolerance from the prescribed motion profile, the actual motion profile of the table may be determined to deviate from the prescribed motion profile of the table. In response to a determination that the actual motion profile of the table deviates from the prescribed motion profile of the table, the table may be locked by the first control sub-system 910 and the table may be in the locked status. In some embodiments, the first control sub-system 910 may assess, based on the received time information, whether the clock of the table controller 930 is synchronized with the clock of the first control sub-system 910. If it is determined that the clock of the table controller 930 is not synchronized with the clock of the first control sub-system 910, a fault flag may be generated. Further, the first control sub-system 910 may synchronize the clock of the table controller 930 with the clock of the first control sub-system 910. Alternatively, the first control sub-system 910 may transmit its own time information to the table controller 930 to make the table controller 930 to synchronize its own clock with the first control sub-system 910. In some embodiments, whether the clock of the table controller 930 is synchronized with the clock of the first control sub-system 910 may be assessed by the table controller 930 in 1002. No matter which of the table controller 930 and the first control sub-system 910 verifies the clock synchronization status, in some embodiments, the table controller 930 may synchronize its own clock with the clock of the first control sub-system 910 that is controlling the table; in some embodiments, the first control sub-system 910 that is controlling the table may synchronize its own clock with the clock of the table controller 930.

In 1012, in response to a determination that the table is under control of the second control sub-system 920, the movement information of the table may be transmitted, by the table controller 930, to the second control sub-system 920. In some embodiments, a portion of the information relating to the motion status of the table may be transmitted to the first control sub-system 910. For example, the current position of the table may not be transmitted to the first control sub-system 910 while the control status of the table (e.g., the table is controlled by the second control sub-system 920) may be transmitted to the first control sub-system 910. In some embodiments, the time information associated with the table controller 930 may be transmitted from the table controller 930 to the second control sub-system 920. In some embodiments, the movement information of the table and the time information associated with the table controller 930 may be included in a data packet, and the data packet may be transmitted from the table controller 930 to the second control sub-system 920.

If the second device is controlling the table, the second control sub-system 920 may receive the movement information of the table, and/or the time information associated with the table controller 930. In some embodiments, the second control sub-system 920 may assess whether an actual motion profile (or a portion thereof (e.g., an actual trajectory)) of the table is in accordance with the prescribed motion profile (or a portion thereof (e.g., the prescribed trajectory)) of the table. More descriptions regarding the determination of whether the actual motion profile of the table is in accordance with the prescribed motion profile of the table may be described elsewhere in the present disclosure (e.g., FIGS. 5-8 and descriptions thereof) and may not be repeated herein. In response to a determination that the actual motion profile of the table deviates from the prescribed motion profile of the table, the table may be locked by the second control sub-system 920 and thus the table may be in the locked status. In some embodiments, the second control sub-system 920 may assess, based on the received time information, whether the clock of the table controller 930 is synchronized with the clock of the second control sub-system 920. If it is determined that the clock of the table controller 930 is not synchronized with the clock of the second control sub-system 920, a fault flag may be generated. Further, the second control sub-system 920 may synchronize the clock of the table controller 930 with the clock of the second control sub-system 920. Alternatively, the second control sub-system 920 may transmit its own time information to the table controller 930 to make the table controller 930 to synchronize its own clock with the second control sub-system 920. In some embodiments, whether the clock of the table controller 930 is synchronized with the clock of the second control sub-system 920 may be assessed by the table controller 930 in 1004. No matter which of the table controller 930 and the second control sub-system 920 verifies the clock synchronization status, in some embodiments, the table controller 930 may synchronize its own clock with the clock of the second control sub-system 920 that is controlling the table; in some embodiments, the second control sub-system 920 that is controlling the table may synchronize its own clock with the clock of the table controller 930.

It should be noted that the above description of the process 1000 is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, if the second device is in its working condition, operations 1002 and 1010 may be omitted. As another example, if the first device is in its working condition, operations 1004 and 1012 may be omitted. In some embodiments, before operation 1002 or 1004, an initialization operation may be performed on the system 900 to synchronize the clock of the first control sub-system 910, the clock of the second control sub-system 920, and/or the clock of the table controller 930. In some embodiments, the synchronization may be performed only once when the system 900 is initialized, and time information may not be transmitted between the first control sub-system 910 (or the second control sub-system 920), and/or the table controller 930 in the image acquisition phase(s), and/or the radiation treatment delivery phase(s). In some embodiments, time information may be transmitted from the table controller 930 to the first control sub-system 910 (or the second control sub-system 920) only if the clock of the table controller 930 is not synchronized with the clock of the first control sub-system 910 (or the clock of the second control sub-system 920).

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2103, Perl, COBOL 2102, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A system for controlling movement of a table supporting an object, comprising:
   a first control sub-system configured to generate a first control instruction;
   a second control sub-system configured to generate a second control instruction;
   a table control sub-system operably coupled to the table; and
   a master controller configured to
   receive the first control instruction from the first control sub-system, or the second control instruction from the second control sub-system,
   generate a third control instruction based on the first control instruction or the second control instruction, and
   transmit the third control instruction to the table control sub-system,
   wherein the table control sub-system is configured to
   generate a control signal based on the third control instruction, and
   cause the table to move based on the control signal,
   wherein the first control sub-system is operably connected to the second control sub-system via a virtual table motion controller,
   the virtual table motion controller is configured to relay the first control instruction from the first control sub-system to the second control sub-system; and
   the second control sub-system is configured to relay the first control instruction to the master controller.

2. The system of claim 1, wherein
   the first control sub-system is further configured to transmit first clock synchronization information associated with the first control sub-system to the master controller; and
   the master controller is further configured to update time information associated with the master controller according to the first clock synchronization information.

3. The system of claim 1, wherein
   the second control sub-system is further configured to transmit second clock synchronization information associated with the second control sub-system to the master controller; and
   the master controller is further configured to update time information associated with the master controller according to the second clock synchronization information.

4. The system of claim 1, wherein
   the first control sub-system is operably coupled to a first device,
   the second control sub-system is operably coupled to a second device, and
   the table is configured to move between the first device and the second device.

5. The system of claim 4, wherein
   the first device is an imaging device, and the second device is a treatment device, or
   the first device is an imaging device of a first modality, and the second device is an imaging device of a second modality, the first modality being different from the second modality.

6. The system of claim 1, wherein the first control sub-system and the master controller have a point-to-point connection.

7. The system of claim 6, wherein the point-to-point connection includes a peripheral component interconnect express (PCIE) connection.

8. The system of claim 6, wherein a latency time between the master controller and the first control sub-system is less than 10 microseconds.

9. The system of claim 6, wherein the table control sub-system is further configured to
   determine movement information of the table; and
   transmit the movement information to the master controller.

10. The system of claim 9, wherein the master controller is further configured to
    transmit the movement information to the second control sub-system.

11. The system of claim 9, wherein the second control sub-system is further configured to
    determine whether the table is under a control of the first control sub-system;
    in response to determining that the table is under the control of the first control sub-system, transmit the movement information to the first control sub-system via the point-to-point connection.

12. The system of claim 1, wherein
    the master controller is a virtual master node, the first control sub-system is operably connected to the second control sub-system or the master controller via a virtual table motion controller.

* * * * *